US008657748B2

(12) United States Patent
Nitta et al.

(10) Patent No.: US 8,657,748 B2

(45) Date of Patent: Feb. 25, 2014

(54) BLOOD VESSEL FUNCTION INSPECTING APPARATUS

(75) Inventors: Naotaka Nitta, Tsukuba (JP); Hiroshi Masuda, Nagoya (JP)

(73) Assignees: National Institute of Advanced Industrial Science and Technology, Tokyo (JP); Unex Corporation, Nagoya (JP)

( * ) Notice: Subject to any disclaimer, the term of this patent is extended or adjusted under 35 U.S.C. 154(b) by 0 days.

(21) Appl. No.: 13/377,329

(22) PCT Filed: Jun. 9, 2009

(86) PCT No.: PCT/JP2009/060563

§ 371 (c)(1), (2), (4) Date: Dec. 14, 2011

(87) PCT Pub. No.: WO2010/143272

PCT Pub. Date: Dec. 16, 2010

(65) Prior Publication Data

US 2012/0089020 A1 Apr. 12, 2012

(51) Int. Cl.

| | |
|---|---|
| ***A61B 8/00*** | (2006.01) |
| ***A61B 5/02*** | (2006.01) |

(52) U.S. Cl.

USPC ............................ 600/438; 600/437; 600/481

(58) Field of Classification Search

USPC .......... 600/438, 437, 481, 504, 508; 382/128; 73/53.04, 54.01

See application file for complete search history.

(56) References Cited

U.S. PATENT DOCUMENTS

| | | | | |
|---|---|---|---|---|
| 4,964,847 | A * | 10/1990 | Prince | 604/6.06 |
| 2008/0075344 | A1 * | 3/2008 | Nambu et al. | 382/131 |
| 2010/0261648 | A1 * | 10/2010 | Cho | 514/7.7 |

FOREIGN PATENT DOCUMENTS

| | | |
|---|---|---|
| JP | A-2003-144395 | 5/2003 |
| JP | A-2006-166974 | 6/2006 |
| JP | B2-3785084 | 6/2006 |
| JP | A-2007-175127 | 7/2007 |

OTHER PUBLICATIONS

Nitta et al., "Intravascular Shear Stress Imaging Based on Ultrasonic Velocity Vector Measurement", Ultrasonics Symposium, 2005 IEEE, Sep. 18-21, 2005, pp. 520-523.*

Wells et al., "Influence of Flow Properties of Blood Upon Viscosity-Hematocrit Relationships", Journal of Clinical Investigation, vol. 41, No. 8, 1962, pp. 1591-1598.*

(Continued)

*Primary Examiner* — Long V. Le

*Assistant Examiner* — Katherine Fernandez

(74) *Attorney, Agent, or Firm* — Oliff PLC

(57) ABSTRACT

A blood vessel function inspecting apparatus including a first blood state index value calculating portion that obtains estimated hematocrit values at a plurality of points predetermined within a blood vessel, on the basis of values of a blood viscosity and values of a shear rate at said plurality of points, which are respectively extracted from a viscosity distribution and a shear rate distribution, and according to reference relationships between a hematocrit value and the blood viscosity, which reference relationships respectively correspond predetermined different values of the shear rate; and a second blood state index value calculating portion that calculates, as said blood state index value, a value relating to an amount of difference of the estimated hematocrit values at said plurality of points with respect to each other, which amount is minimized by transforming said reference relationships at the same ratio for all of the values of the shear rate.

8 Claims, 13 Drawing Sheets

(56) References Cited

OTHER PUBLICATIONS

Nitta et al.; "Hemodynamic Force Imaging Based on Ultrasonic Blood Flow Management;" *Papers of Technical Meeting on Magnetics*; Dec. 12, 2006; pp. 13-19 (with Abstract).

International Search Report dated Aug. 4, 2009 in International Application No. PCT/JP2009/060563 (with translation).

* cited by examiner

22
ROTATION
ABOUNT $y_0$ AXIS
24
B
$a_n$
A
C
$a_1$
ROTATION
ABOUT $z_0$ AXIS
$x_0$ AXIS
20
$z_0$ AXIS
$y_0$ AXIS

20
$L_3$
$L_2$
$L_1$
$d_1$
111

BLOOD VESSEL LUMEN DIAMETER di
dMAX
da
t1
t2
t3
TIME

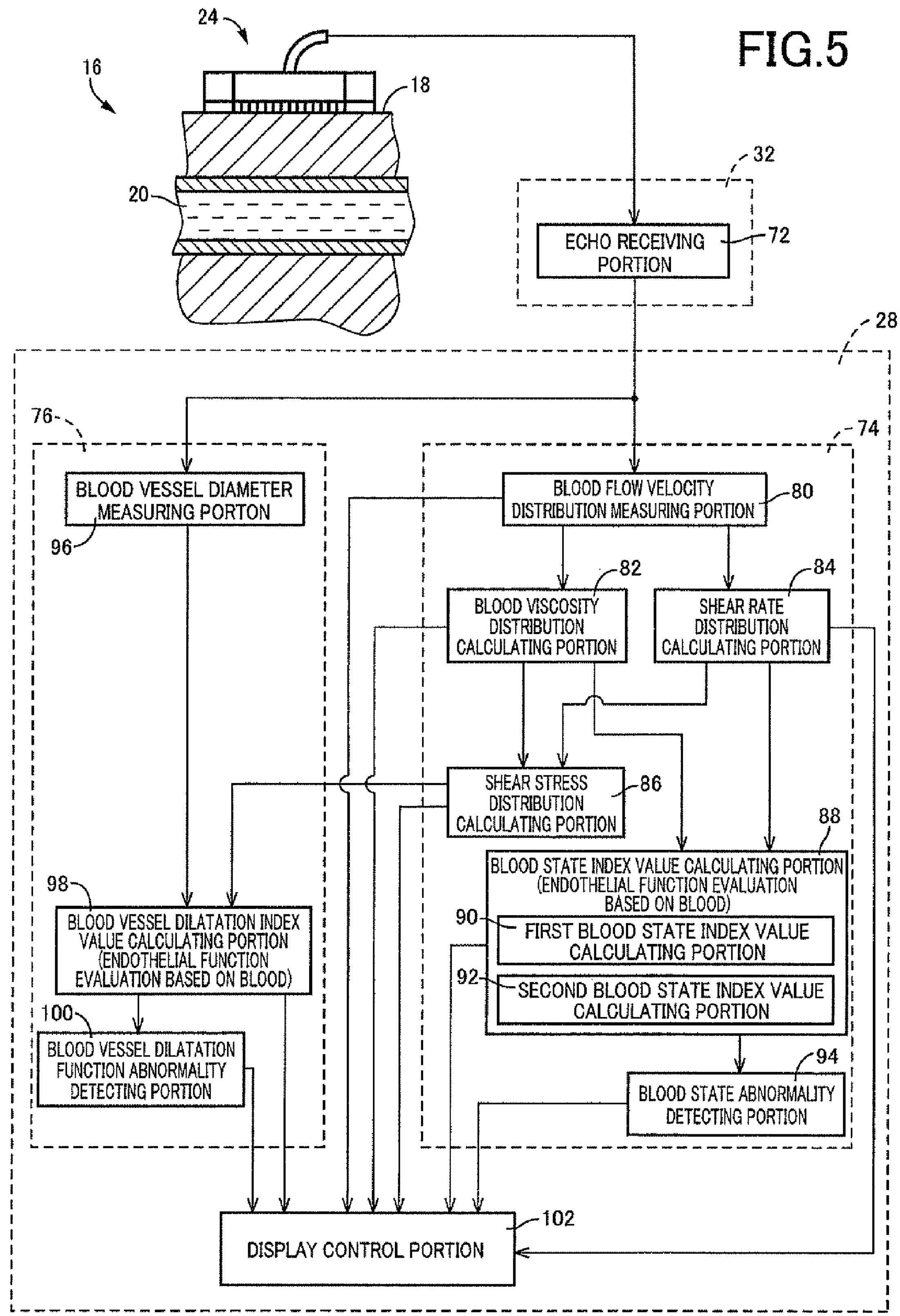
FIG.5
24
16
18
20
32
ECHO RECEIVING PORTION
72
28
76
74
BLOOD VESSEL DIAMETER MEASURING PORTON
96
BLOOD FLOW VELOCITY DISTRIBUTION MEASURING PORTION
80
82
84
BLOOD VISCOSITY DISTRIBUTION CALCULATING PORTION
SHEAR RATE DISTRIBUTION CALCULATING PORTION
SHEAR STRESS DISTRIBUTION CALCULATING PORTION
86
88
BLOOD STATE INDEX VALUE CALCULATING PORTION (ENDOTHELIAL FUNCTION EVALUATION BASED ON BLOOD)
90
FIRST BLOOD STATE INDEX VALUE CALCULATING PORTION
92
SECOND BLOOD STATE INDEX VALUE CALCULATING PORTION
98
BLOOD VESSEL DILATATION INDEX VALUE CALCULATING PORTION (ENDOTHELIAL FUNCTION EVALUATION BASED ON BLOOD)
100
BLOOD VESSEL DILATATION FUNCTION ABNORMALITY DETECTING PORTION
94
BLOOD STATE ABNORMALITY DETECTING PORTION
DISPLAY CONTROL PORTION
102

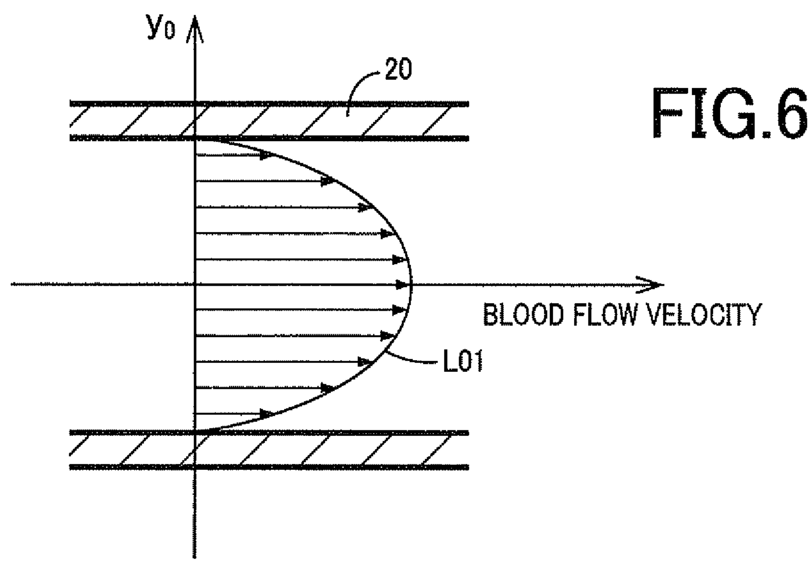
FIG.6
FIG.7
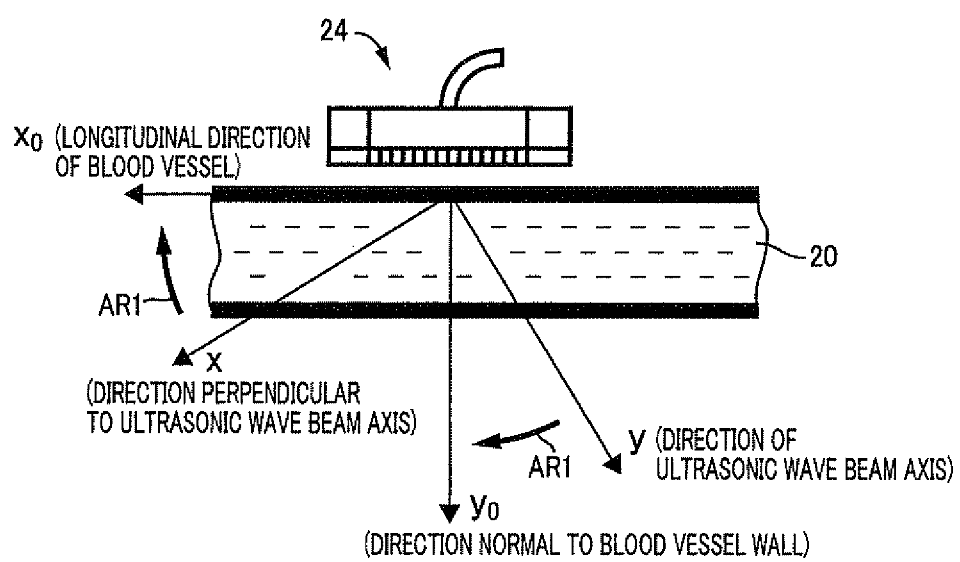

BLOOD VISCOSITY
μA
μB
μC
L06
L07
Ht0
SRA
SRB
SRC
BLOOD SHEAR RATE

BLOOD VESSEL FUNCTION INSPECTING APPARATUS

TECHNICAL FIELD

The present invention relates to techniques for non-invasion evaluation of a blood state of a live body.

BACKGROUND ART

There is know a blood vessel function inspecting apparatus for measuring a blood flow velocity distribution within a blood vessel, by ultrasonic Doppler effect measurement. Patent Document 1 discloses an example of such a blood vessel function inspecting apparatus. The blood vessel function inspecting apparatus disclosed in this Patent Document 1 is configured to calculate a blood viscosity distribution and a blood shear rate distribution within the blood vessel, on the basis of the blood flow velocity distribution measured as described above. The blood vessel function inspecting apparatus is further configured to calculate a blood shear stress distribution on the basis of the calculated blood viscosity distribution and blood shear rate distribution. The calculation of the above-described blood viscosity distribution by the blood vessel function inspecting apparatus on the basis of the above-described blood flow velocity distribution is implemented by calculation according to the well known Navier-Stokes equations.

PRIOR ART DOCUMENTS

Patent Documents

Patent Document 1: JP-2006-166974 A

SUMMARY OF THE INVENTION

Object Achieved by the Invention

Certainly, the measurement of the above-described blood flow velocity distribution, viscosity distribution, shear rate distribution and shear stress distribution in the non-invasion manner is effective for medical diagnosis. For practical utilization of the results of measurement for clinical purposes, however, there has been a need of converting the blood state into quantitative index values (such as hematocrit value). It is noted here that this need is not known.

The present invention was made in view of the background art described above. It is accordingly an object of this invention to provide a blood vessel function inspecting apparatus which is capable of obtaining the index values permitting evaluation of the blood state in the non-invasion manner, by measuring the blood flow velocity distribution within the blood vessel.

Means for Achieving the Object

The object indicated above is achieved according to the invention, which provides a blood vessel function inspecting apparatus for (a) calculating a viscosity distribution and a shear rate distribution of a blood within a blood vessel of a live body on the basis of a flow velocity distribution of the blood measured in a non-invasion manner with ultrasonic waves percutaneously incident upon the above-described blood vessel, and calculating a blood state index value permitting evaluation of a state of the blood, on the basis of the above-described viscosity distribution and the above-described shear rate distribution, characterized by comprising (b) first blood state index value calculating means for obtaining estimated hematocrit values at a plurality of points predetermined within the above-described blood vessel, on the basis of values of a blood viscosity and values of a shear rate at the above-described plurality of points, which are respectively extracted from the above-described viscosity distribution and the above-described shear rate distribution, and according to reference relationships between a hematocrit value and the blood viscosity, which reference relationships respectively correspond to predetermined different values of the shear rate, and (c) second blood state index value calculating means for calculating, as the above-described blood state index value, a value relating to an amount of difference of the estimated hematocrit values at the above-described plurality of points with respect to each other, which amount is minimized by transforming the above-described reference relationships at the same ratio for all of the values of the shear rate.

Advantages of the Invention

According to the present invention described above, it is possible to obtain the above-described blood state index value permitting the blood state evaluation, such as a index value equivalent to the hematocrit value, in the non-invasion manner, to permit objective and easy evaluation of the blood state.

Preferably, the value relating to the minimized amount of difference of the estimated hematocrit values at the above-described plurality of points is an average of the estimated hematocrit values at said plurality of points. In this case, it is possible to obtain, in the non-invasion manner, an index value equivalent to the hematocrit value conventionally used for clinical purposes.

Also preferably, (a) the above-described second blood state index value calculating means calculates, as the above-described blood state index value, an average of differences of the estimated hematocrit values at the above-described plurality of points with respect to a predetermined reference hematocrit value when the amount of difference of the estimated hematocrit values at the plurality of points is minimized, (b) the above-described blood vessel function inspecting apparatus comprising blood state abnormality detecting means for determining that the above-described blood state is abnormal, if the average of the differences of the estimated hematocrit values at the above-described plurality of points with respect to the above-described reference hematocrit value is larger than a threshold value. In this case, the determination as to whether the above-described blood state is abnormal or not can be made more easily than in the case where the above-described blood state abnormality detecting means is not provided.

Also preferably, the above-described second blood state index value calculating means transforms the above-described reference relationships at the same ratio for all of the values of the shear rate, by changing relationship equations respectively defining the above-described reference relationships corresponding to the respective different values of the shear rate, with a same coefficient, and determines, as the above-described blood state index value, the above-described coefficient when the amount of difference of the estimated hematocrit values at the above-described plurality of points is minimized. In this case, the blood state as seen from factors other than the hematocrit value, such as plasma protein concentration, which influence the blood viscosity, can be evaluated on the basis of the above-described blood state index value (coefficient).

Also preferably, the above-described blood vessel function inspecting apparatus comprises blood viscosity distribution calculating means for calculating the above-described viscosity distribution on the basis of the above-described flow velocity distribution of the blood, and according to a two-dimensional or three-dimensional Navier-Stokes equation stored in a memory. In this case, the present invention is applicable to the blood vessel function inspecting apparatus which is practically operable.

Also preferably, the above-described blood vessel function inspecting apparatus comprises (a) blood vessel diameter measuring means for measuring a change ratio of a diameter of the above-described blood vessel after releasing of the blood vessel from blood flow obstruction, concurrently with the measurement of the above-described flow velocity distribution of the blood within the above-described blood vessel with the above-described ultrasonic waves incident upon the blood vessel, (b) shear stress calculating means for calculating a shear stress distribution on the basis of the above-described viscosity distribution and the above-described shear rate distribution of the blood, and (c) blood vessel dilatation index value calculating means for calculating a ratio between a maximum value of the shear stress within the above-described shear stress distribution and a maximum value of the above-described change ratio of the diameter of the blood vessel, as a blood vessel dilation index value permitting evaluation of a dilatation function of the blood vessel. In this case, it is possible to evaluate a result of measurement of the above-described change ratio of the diameter of the blood vessel, on the basis of the above-described shear stress of the blood.

Also preferably, the above-described blood vessel function inspecting apparatus comprises blood vessel dilatation function abnormality detecting means for determining that the above-described dilatation function of the blood vessel is abnormal, if the above-described blood vessel dilation index value is outside a predetermined normal range. In this case, the determination as to whether the above-described blood vessel dilatation function is abnormal or not can be made more easily than in the case where the above-described blood vessel dilatation function abnormality detecting means is not provided.

Also preferably, (a) an ultrasonic probe which irradiates the above-described ultrasonic waves toward the above-described blood vessel is provided with a longitudinal ultrasonic detector array having a plurality of ultrasonic oscillators arranged linearly in a longitudinal direction of the above-described blood vessel, and a transverse ultrasonic detector array having a plurality of ultrasonic oscillators arranged linearly in a direction perpendicular to the longitudinal direction of the above-described blood vessel, and (b) the above-described flow velocity distribution of the blood is measured with the ultrasonic waves irradiated from the above-described longitudinal ultrasonic detector array, and the change ratio of the diameter of said blood vessel is measured with the ultrasonic waves irradiated from the above-described transverse ultrasonic detector array. In this case, it is possible to implement the measurement of the above-described flow velocity distribution of the blood and the measurement of the change ratio of the diameter of the above-described blood vessel, concurrently with each other, by using the ultrasonic probe practically used in the art. For example, the concurrent measurements of the above-described flow velocity distribution of the blood and the change ratio of the diameter of the above-described blood vessel can be implemented by alternately operating the above-described longitudinal ultrasonic detector array and the above-described transverse ultrasonic detector array, with an extremely short cycle time.

Also preferably, (a) an ultrasonic probe which irradiates the above-described ultrasonic waves toward the above-described blood vessel is provided with a longitudinal ultrasonic detector array having a plurality of ultrasonic oscillators arranged linearly in a longitudinal direction of the above-described blood vessel, and (b) an operation of the above-described longitudinal ultrasonic detector array to measure the flow velocity distribution of the blood and an operation of the longitudinal ultrasonic detector array to measure the change ratio of the diameter of the above-described blood vessel are alternately performed with time. In this case, it is possible to implement the measurement of the above-described flow velocity distribution of the blood and the measurement of the change ratio of the diameter of the above-described blood vessel, concurrently with each other, by using the ultrasonic probe practically used in the art. For example, the concurrent measurements of the above-described flow velocity distribution of the blood and the change ratio of the diameter of the above-described blood vessel can be implemented by alternately operating the above-described longitudinal ultrasonic detector array and the above-described transverse ultrasonic detector array, with an extremely short cycle time.

BRIEF DESCRIPTION OF THE DRAWINGS

FIG. 5 is a functional block diagram for explaining major control functions of the blood vessel function inspecting apparatus of FIG. 1;

FIG. 6 is an illustrative view indicating a blood flow velocity distribution to be measured by blood flow velocity distribution measuring means provided in the blood vessel function inspecting apparatus of FIG. 5;

FIG. 7 is a view for explaining reference characters in an equation used for calculating the blood flow velocity distribution to be measured by the blood flow velocity distribution measuring means provided in the blood vessel function inspecting apparatus of FIG. 5;

MODE FOR CARRYING OUT THE INVENTION

An embodiment of the present invention will be described in detail by reference to the drawings.

Embodiment 1

Figure 1:
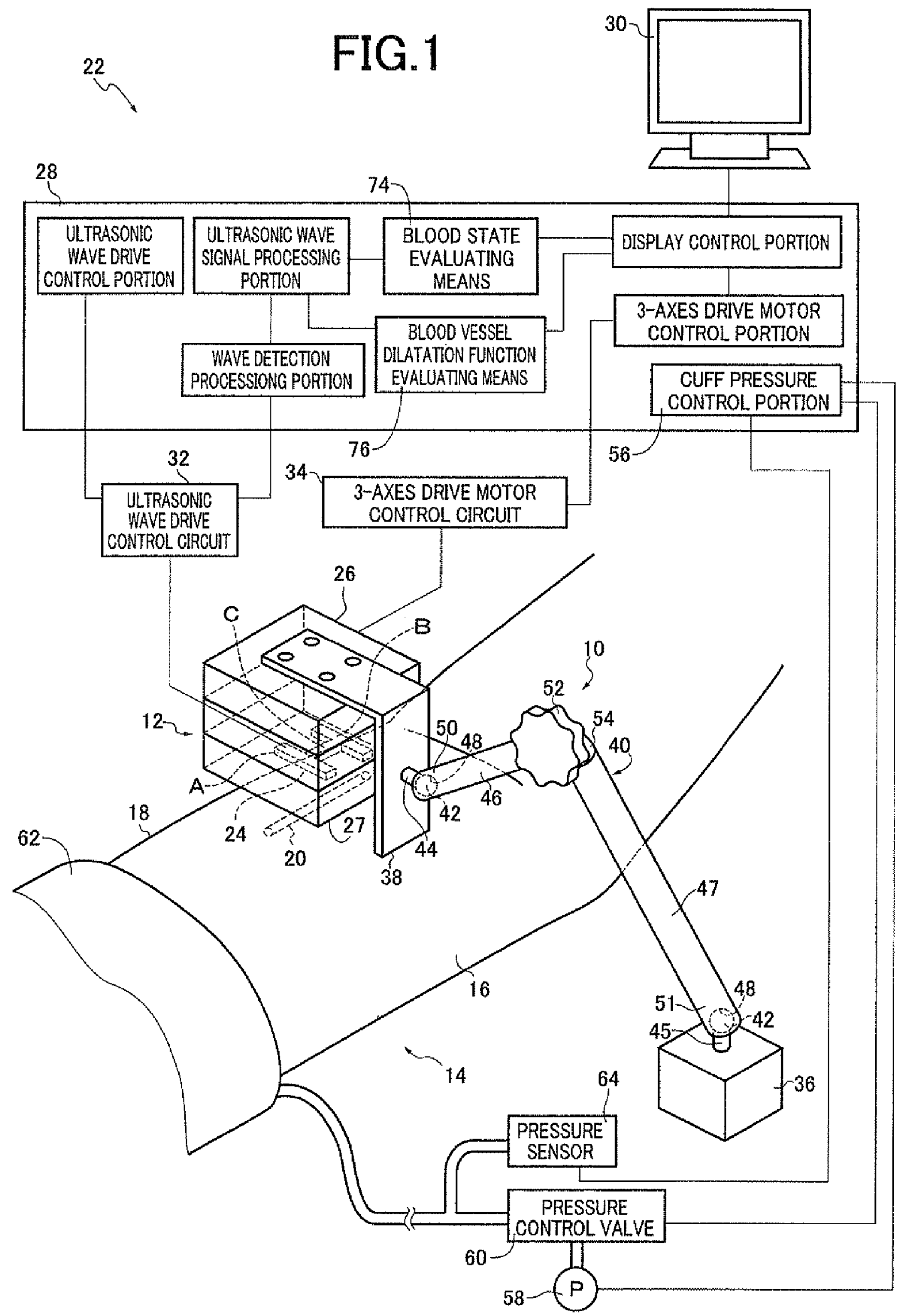
FIG. 1 is a view showing an overall arrangement of a blood vessel function inspecting apparatus according to one embodiment of this invention.

FIG. 1 is the view showing an overall arrangement of a blood vessel function inspecting apparatus 22 configured to measure a blood flow velocity distribution within a blood vessel 20 immediately below a skin 18 of a brachium 16 of a live body 14, and a diameter of the blood vessel 20, through the skin 18, using a hybrid probe unit 12 held by a sensor holder 10.

The hybrid probe unit 12, which functions as a sensor for detecting vital body information relating to the blood vessel 20, that is, blood vessel parameters, is provided with an H-type ultrasonic probe 24, and a multi-axes drive device (positioning device) 26 for positioning the ultrasonic probe 24. The ultrasonic probe 24 has a pair of mutually parallel detector arrays consisting of a first short-axis ultrasonic detector array A and a second short-axis ultrasonic detector array B, and a long-axis ultrasonic detector array C which connects the first and second short-axis ultrasonic arrays A and B at longitudinally intermediate portions thereof. The ultrasonic detector arrays A, B and C lie on one plane, namely, on a flat detection plane 27. Each of the first short-axis ultrasonic detector array A, second short-axis ultrasonic detector array B, and long-axis ultrasonic detector array C is an elongate member having a multiplicity of ultrasonic oscillators (vibrators) $a_1$-$a_n$ which are formed of a piezoelectric ceramic material and which are arranged linearly. It will be understood that the first short-axis ultrasonic detector array A corresponds to a transverse ultrasonic detector array according to the invention, while the long-axis ultrasonic detector array C corresponds to a longitudinal ultrasonic detector array according to the invention.

Figure 2:
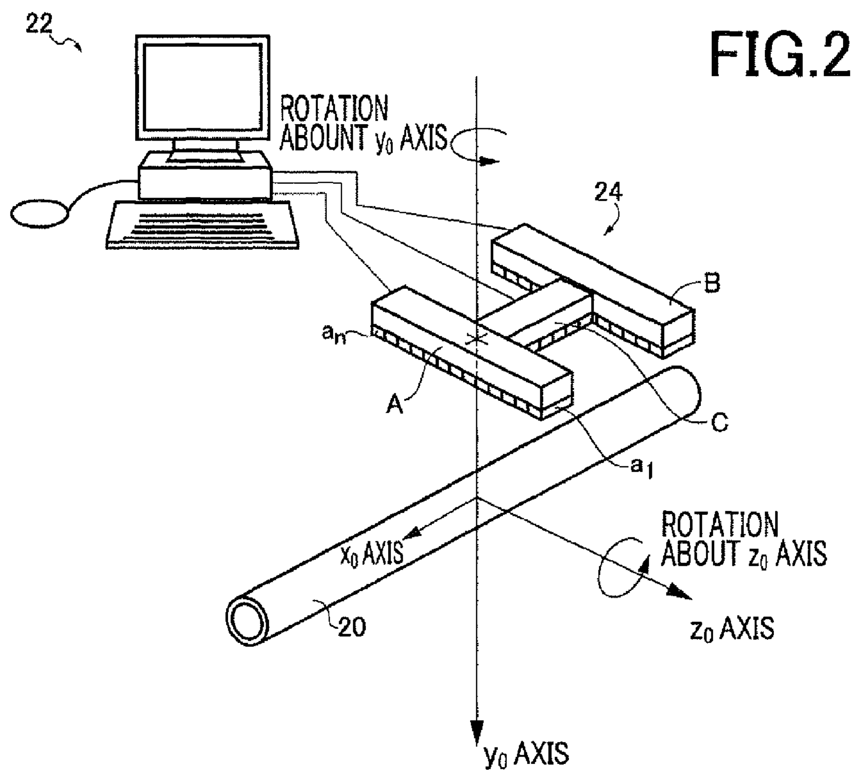
FIG. 2 is a view for explaining rectangular coordinate axes $x_0$, $y_0$ and $z_0$ for indicating an attitude of an ultrasonic probe used by the blood vessel function inspecting apparatus of FIG. 1, with respect to the blood vessel.

FIG. 2 is the view for explaining $x_0$, $y_0$ and $z_0$ axes of a rectangular coordinate system used in the present embodiment. The axis $z_0$ is parallel to the longitudinal direction of the first short-axis ultrasonic detector array A, and located right below the first short-axis ultrasonic detector array A, and passes a vertical position of the blood vessel 20 or a point vertically close to that vertical position. The $x_0$ axis is parallel to the longitudinal direction of the long-axis ultrasonic detector array C, and is perpendicular to the $z_0$ axis, while the $y_0$ axis passes a point of intersection between the longitudinal direction of the first short-axis ultrasonic detector array A and the longitudinal direction of the long-axis ultrasonic detector array C, and is perpendicular to the above-described $x_0$ and $z_0$ axes. The ultrasonic probe 24 is translated along the $x_0$ axis and rotated about the $y_0$ and $z_0$ axes by the multi-axes drive device 26.

Figure 3:
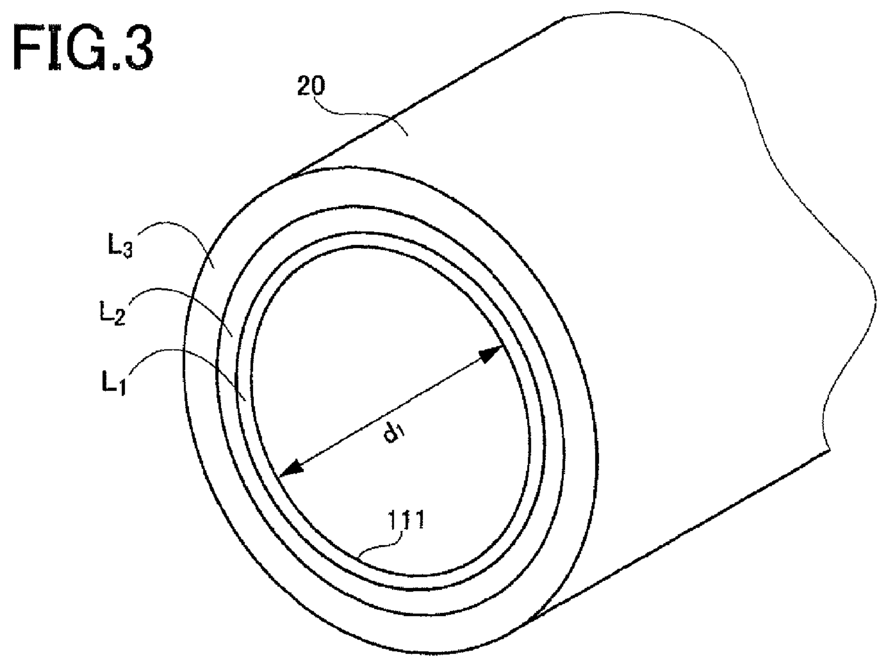
FIG. 3 is an enlarged view for explaining a multi-layered structure of the blood vessel which is a subject irradiated with an ultrasonic wave generated by the ultrasonic probe of FIG. 2.

As shown in FIG. 3, the blood vessel 20 which is a arterial vessel of the brachium, for instance, has a three-layered structure consisting of an inner layer $L_1$, an intermediate layer $L_2$ and an outer layer $L_3$. Since the reflection of an ultrasonic wave takes place in boundary portions having different values of acoustic impedance, a boundary surface between the blood in the lumen of the blood vessel and the inner layer $L_1$, and a boundary surface between the intermediate layer $L_2$ and the outer layer $L_3$ are displayed as white regions, and the tissue is displayed by white and black spots. Although the boundary surface between the blood and the inner layer $L_1$ is difficult to be displayed in an image, it is preferable to measure a distance in the image as a diameter of the blood vessel and obtain a change ratio of the diameter, namely, a dilatation ratio R of the diameter of the lumen.

Referring back to FIG. 1, the blood vessel function inspecting apparatus 22 is provided with an electronic control device 28, a monitoring image display device (image display device) 30, an ultrasonic wave drive control circuit 32, and a 3-axes drive motor control circuit 34. The electronic control device 28 is constituted by a so-called microcomputer having a CPU operable to process input signals according to programs stored in a ROM, while utilizing a temporary data storage function of a RAM. The above-described electronic control device 28 is configured to command the ultrasonic wave drive control circuit 32 to apply drive signals to the first short-axis ultrasonic detector array A, second short-axis ultrasonic detector array B and long-axis ultrasonic detector array C of the ultrasonic probe 24 of the hybrid probe unit 12, for irradiating ultrasonic waves. The irradiated ultrasonic waves are reflected as reflected ultrasonic signals, which are detected by the first and second short-axis ultrasonic detector arrays A, B and long-axis ultrasonic detector array C. The reflected ultrasonic signals are processed to generate ultrasonic images of a tissue under the skin 18, and the ultrasonic images are displayed on the monitoring image display device 30.

The monitoring image display device 30 is configured to display the ultrasonic image obtained by the first short-axis ultrasonic detector array A, the ultrasonic image obtained by the second short-axis ultrasonic detector array B, and the ultrasonic image obtained by the long-axis ultrasonic detector array C, in respective image display regions. These image display regions have a common vertical axis along which a depth dimension from the skin 18 is indicated.

The monitoring image display device 30 is further configured to chronologically display the change ratio of the diameter of the inner layer, that is, the dilatation ratio R of the lumen, for FMD (Flow Mediated vasoDilation reaction) evaluation.

Upon the above-described FMD evaluation and generation of the ultrasonic images of the blood vessel 20, the ultrasonic probe 24 is positioned in a predetermined measuring position with respect to the blood vessel 20, by the multi-axes drive device 26 which is operated according to the drive signals received from the 3-axes drive motor control circuit 34 under the control of the electronic control device 28. In the predetermined measuring position, the first short-axis ultrasonic detector array A and the second short-axis ultrasonic detector array B are perpendicular to the blood vessel 20, while the long-axis ultrasonic detector array C is parallel to the blood vessel 20. In the predetermined measuring position, the diameter of the blood vessel 20 appears in the longitudinal cross section image of the blood vessel 20 obtained by the long-axis ultrasonic detector array C.

The sensor holder 10 is constructed to hold the hybrid probe unit 12 so as to have a predetermined attitude in a predetermined position in a three-dimensional spaced, that is, in the predetermined measuring position, such that the hybrid probe unit 12 is held in contact with the skin 18 of the brachium 16 of the live body 14, with a low pressure not to cause deformation of the blood vessel 20 immediately below the skin 18. Between the contact surface of the ultrasonic probe 24 of the hybrid probe unit 12 and the skin 18, there is usually interposed a well known coupling agent such as jelly, to reduce attenuation of the ultrasonic wave, and reflection and scattering of the ultrasonic wave at the boundary surfaces, for thereby obtaining clear ultrasonic images. This jelly is a gel-like water absorptive high molecular material which has a high content of aqueous components such as agar, and a sufficiently higher degree of natural impedance (sound velocity×density) than air, making it possible to reduce the attenuation of transmitted and received ultrasonic wave signals. The jelly may be replaced by a resin bag charged with water, an olive oil, or glycerin.

The above-described sensor holder 10 is provided with a magnet stand 36, unit fixture 38, connecting members 44, 45, and a universal arm 40. The magnet stand 36 is fixed with a magnetic attraction force, for example, to a desk or a pedestal, and the above-described hybrid probe unit 12 is fixed to the unit fixture 38. The connecting members 44, 45 are fixed at one end thereof to the magnet stand 36 and the unit fixture 38, respectively, and have spherical distal end portions 42. The universal arm 40 connects the magnet stand 36 and the unit fixture 38 to each other through the connecting members 44, 45 and supports the magnet stand 36 and unit fixture 38, such that the magnet stand 36 and the unit fixture 38 are movable relative to each other. The universal arm 40 has two links 46, 47 pivotably connected to each other, universal joint portions 50, 51 having respective engaging holes 48, and a pivotal joint portion 54. The engaging hole 48 is formed in one end portion of each of the two links 46, 47, and the above-described spherical distal end portion 42 is universally fitted in the engaging hole 48, with a predetermined force of resistance to universal motions of the links 46, 47 relative to the spherical distal end portion 42. The two links 46, 47 are pivotably connected to each other at the other end portions by the pivotal joint portion 54, which has a fixing knob 52 provided with an externally threaded portion screwed in tapped holes formed through the above-indicated other end portions of the links 46, 47, so that pivotal motions of the two links 46, 47 are prevented when the fixing knob 52 is tightened.

The multi-axes drive device 26 consists of a $z_0$-axis rotating (yawing) mechanism fixed to the unit fixture 38 and having a $z_0$-axis rotating actuator to rotate the ultrasonic probe 24 about the $z_0$ axis, $x_0$-axis translating mechanism having an $x_0$-axis translating actuator to translate the ultrasonic probe 24 along the $x_0$ axis and a $y_0$-axis rotating mechanism having a $y_0$-axis rotating actuator to rotate the ultrasonic probe 24 about the $y_0$ axis.

The ultrasonic wave drive control circuit 32 shown in FIG. 1 is commanded by the electronic control device 28 to drive the multiplicity of linearly arranged ultrasonic oscillators (vibrators) $a_1$-$a_n$ of the above-described first short-axis ultrasonic detector array A, for example, such that a group of a predetermined number of the ultrasonic oscillators, for example, a group of the 15 ultrasonic oscillators $a_1$-$a_{15}$ are concurrently driven at a frequency of about 10 MHz, with a predetermined phase difference, to implement a beam forming operation to successively irradiate ultrasonic wave beams toward the blood vessel 20, such that the ultrasonic wave beams converge in the direction of arrangement of the ultrasonic oscillators. The ultrasonic wave beams are irradiated with the members of the group of the predetermined number of the ultrasonic oscillators being shifted by one oscillator per each beam forming operation, and the thus irradiated ultrasonic wave beams are scanned to detect reflected waves, which are input to the electronic control device 28.

The electronic control device 28 synthesizes an image on the basis of the above-described reflected waves, that is, a transverse cross sectional image (short-axis image) or a longitudinal cross sectional image (long-axis image) of the blood vessel 20 below the skin 18, and displays the image on the monitoring image display device (image display device) 30. Further, the electronic control device 28 calculates the diameter of the blood vessel 20, or an endothelial skin diameter (blood vessel lumen diameter) $d_1$, which is a diameter of an endothelial skin 111, on the basis of the image. In addition, the electronic control device 28 calculates a dilatation ratio (change ratio) R (%) [$=100\times(d_1-d_a)/d_a$] of the blood vessel lumen diameter (having the diameter $d_a$ at rest) of the blood vessel representative of the FMD (Flow Mediated vasoDilation reaction of the blood vessel) after ischemic reaction congestion, for evaluating the function of the endothelial skin 70 of the blood vessel.

Figure 4:
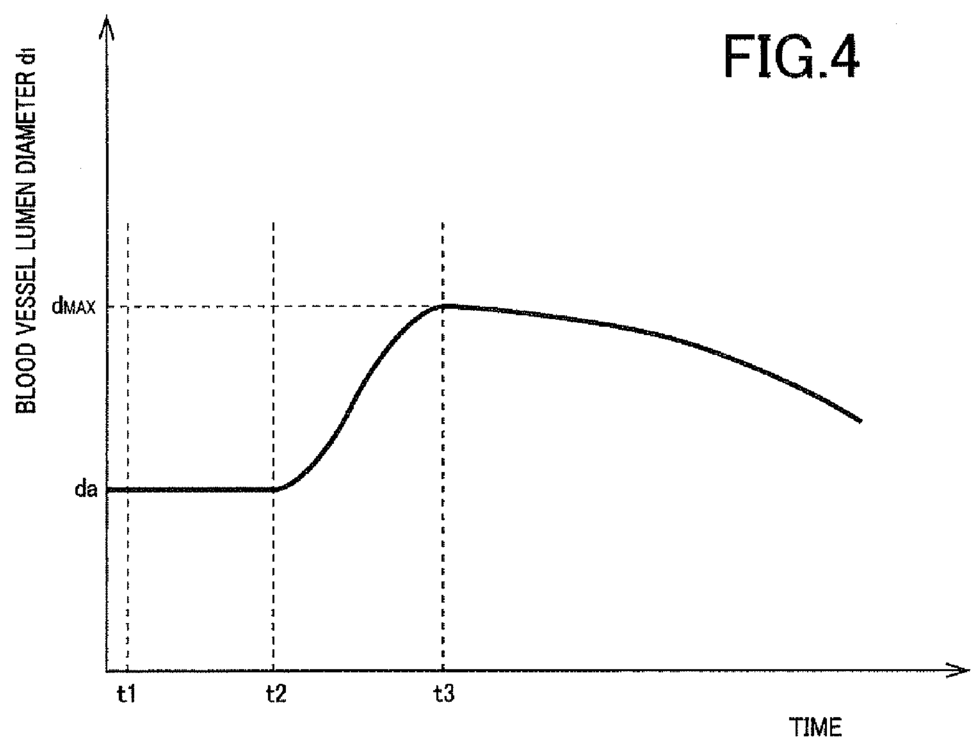
FIG. 4 is a time chart indicating an example of a change of an inside diameter of the blood vessel lumen after releasing of the blood vessel from blood flow obstruction, which is measured with the ultrasonic wave generated from the ultrasonic probe of FIG. 2.

FIG. 4 is the time chart indicating an example of a change of the blood vessel lumen diameter $d_1$ after releasing of the blood vessel from blood flow obstruction (bloodlessness). In the example of FIG. 4, the blood vessel is released from blood flow obstruction, at a point of time t1, and the blood vessel lumen diameter $d_1$ begins to increase at a point of time t2, and reaches a maximum value $d_{MAX}$ at a point of time t3. Thus, the dilatation ratio R of the blood vessel lumen diameter calculated by the electronic control device 28 is maximized at the point of time t3.

The above-described blood flow obstruction for the FMD evaluation is conducted by a cuff 62 which is wound on the brachium 16, as shown in FIG. 1, and an air pressure of which is controlled by a pressure control valve 60 under the control of a cuff pressure control portion 56 (cuff pressure control means 56) of the electronic control device 28. The pressure control valve 60 controls the pressure of pressurized air delivered from a pneumatic pump 58, so that the air pressure of the cuff 62 is raised to a predetermined blood flow obstruction value higher than the systolic blood pressure of the live body 14. The above-described cuff pressure control portion 56 detects the air pressure of the cuff 62 on the basis of an output signal of a pressure sensor 64 provided to detect the air pressure. In the example of FIG. 4, the air pressure of the cuff 62 is kept at the above-described blood flow obstruction value under the control of the cuff pressure control portion 56, for a predetermined length of time before a moment of releasing of the blood vessel from the blood flow obstruction, that is, before the point of time t1, and is abruptly lowered to the atmospheric pressure value at the point of time t1.

The above-described electronic control device 28 shown in FIG. 1 has, in addition to the above-described function, a function of measuring a blood flow velocity distribution DS in a non-invasion manner, with the ultrasonic waves which are irradiated from the long-axis ultrasonic detector array C and which are percutaneously incident upon the blood vessel 20 of the live body 14. Then, the electronic control device 28 calculates a viscosity distribution DV and a shear rate distribution DSR of the blood within the blood vessel 20 on the basis of the measured blood flow velocity distribution DS, and further calculates a shear stress distribution DSS on the basis of the viscosity distribution DV and the shear rate distribution DSR. For instance, the electronic control device 28 can concurrently implement the measurement of the dilatation ratio R of the above-described blood vessel lumen diameter and the measurement of the above-described blood flow velocity distribution DS, by alternately driving the first short-axis ultrasonic detector array A and the long-axis ultrasonic detector array C, with an extremely short cycle time. Alternatively, the electronic control device 28 can concurrently implement the measurement of the above-described blood flow velocity distribution DS and the measurement of the above-described dilatation ratio R of the blood vessel lumen diameter, by alternately repeating an operation of the long-axis ultrasonic detector array C to measure the above-described blood flow velocity distribution DS, and an operation of the same to measure the above-described dilatation ratio R of the blood vessel lumen diameter, with an extremely short cycle time, this measurement is implemented without using the first short-axis ultrasonic detector array A.

FIG. 5 is the functional block diagram for explaining major control functions of the blood vessel function inspecting apparatus 22. As shown in FIG. 5, the ultrasonic wave drive control circuit 32 is provided with an echo receiving portion in the form of echo receiving means 72. The electronic control device 28 is provided with a blood state evaluating portion in the form of blood state evaluating means 74 for performing a processing operation to implement evaluation relating to the blood state, a blood vessel dilatation function evaluating portion in the form of blood vessel dilatation function evaluating means 76 for performing a processing operation to implement evaluation relating to a dilatation function of the blood vessel, and a display control portion in the form of display control means 102. The blood state evaluating means 74 is provided with a blood flow velocity distribution measuring portion in the form of blood flow velocity distribution measuring means 80, a blood viscosity distribution calculating portion in the form of blood viscosity distribution calculating means 82, a shear rate distribution calculating portion in the form of shear rate distribution calculating means 84, a shear stress distribution calculating portion in the form of shear stress distribution calculating means 86, a blood state index value calculating portion in the form of blood state index value calculating means 88, and a blood state abnormality detecting portion in the form of blood state abnormality detecting means 94. Further, the blood vessel dilatation function evaluating means 76 is provided with a blood vessel diameter measuring portion in the form of blood vessel diameter measuring means 96, a blood vessel dilatation index value calculating portion in the form of blood vessel dilatation index value calculating portion 98, and a blood vessel dilatation function abnormality detecting portion in the form of blood vessel dilatation function abnormality detecting means 100.

The echo receiving means 72 is configured to receive reflected waves (echo) of the ultrasonic wave beams generated from the ultrasonic probe 24, and to apply the received reflected waves to the electronic control device 28. For instance, the echo receiving means 72 receives the reflected waves of the ultrasonic wave beam from the first short-axis ultrasonic detector array A, and applies the received reflected waves to the blood vessel diameter measuring means 96. Further, the echo receiving means 72 receives the reflected waves of the ultrasonic wave beam from the long-axis ultrasonic detector array C, and applies the received reflected waves to the blood flow velocity distribution measuring means 80.

The blood flow velocity distribution measuring means 80 is configured to determine the position of the blood vessel 20 by generating a tomographic image on the basis of scattered ultrasonic waves (reflected waves) received by the long-axis ultrasonic detector array C of the ultrasonic probe 24, and at the same time obtain a two-dimensional velocity vector distribution in a two-dimensional tomographic plane. Although the velocity vector distribution to be obtained may be either two-dimensional or three-dimensional, the two-dimensional velocity vector distribution is obtained in the present embodiment, for simplifying the processing operation, and the blood flow velocity distribution measuring means 80 obtains this two-dimensional velocity vector distribution as the blood flow velocity distribution DS. A solid line L01 in the illustrative view of FIG. 6 represents an example of an instantaneous blood flow velocity distribution DS. The two-dimensional velocity vector distribution or three-dimensional velocity vector distribution can be obtained by obtaining a distance of movement of blood cells by a phase correlation method using two ultrasonic tomographic images or three-dimensional volume images (each being chronologically continuous) obtained at a predetermined time interval, and by dividing the obtained distance of movement by the time interval of the two images. Alternatively, the blood flow velocity distribution measuring means 80 can obtained a perfect two-dimensional velocity vector distribution by obtaining a velocity component in the direction of irradiation of the ultrasonic wave (which is one of velocity components of the two-dimensional velocity vector) by a method similar to a well known color Doppler method, then obtaining the other velocity component normal to the obtained one velocity component, using a incompressibility condition in the fluid dynamics as represented by the following Equation (1) stored in memory. As described above, the blood flow velocity distribution measuring means 80 measures the blood flow velocity distribution DS within the blood vessel 20 in the non-invasion manner with the ultrasonic waves which are percutaneously incident upon the blood vessel 20 in the live body 14. Needless to confirm, before the blood flow velocity distribution measuring means 80 implements the measurement of the blood flow velocity distribution DS, the ultrasonic probe 24 is positioned in the above-described predetermined measuring position with respect to the blood vessel 20. As indicated in FIG. 7, "x", "y", "u" and "v" in the following Equation (1) respectively represent: a position in a direction perpendicular to the ultrasonic wave beam axis; a position in the direction of the ultrasonic wave beam axis (in the direction of irradiation of the ultrasonic wave); a velocity component in the x direction; and a velocity component in the direction of the ultrasonic wave beam axis, that is, in the y direction.

[Equation 1]

$$\frac{\partial u}{\partial x} + \frac{\partial v}{\partial y} = 0 \quad (1)$$

The blood flow velocity distribution measuring means 80 may measure the blood flow velocity distribution DS instantaneously at a desired point of time, or chronologically continuously. For the FMD measurement after ischemic reaction congestion, for example, the blood flow velocity distribution measuring means 80 may measure the blood flow velocity distribution DS chronologically continuously concurrently with the measurement of the blood vessel lumen diameter $d_1$ after releasing of the blood vessel from the blood flow obstruction, or instantaneously at the desired point of time.

Figure 8:
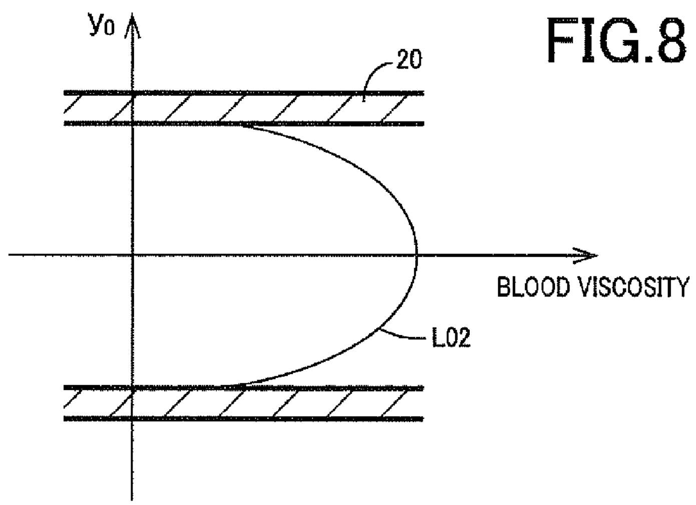
FIG. 8 is an illustrative view indicating a blood viscosity distribution calculated by blood viscosity distribution calculating means provided in the blood vessel function inspecting apparatus of FIG. 5.

The blood viscosity distribution calculating means 82 is configured to calculate the viscosity distribution (blood viscosity distribution) DV of the blood within the blood vessel 20 under measurement, on the basis of the blood flow velocity distribution DS measured by the blood flow velocity distribution measuring means 80, and according to two-dimensional Navier-Stokes equations stored in memory, which are represented by the following Equations (2) and (3). A solid line L02 in the illustrative view of FIG. 8 indicates an example of the instantaneous blood viscosity distribution DV, which has non-Newton characteristics of the blood. For quantitative determination of the viscosity μ of the blood, the blood viscosity distribution calculating means 82 calculates an average value of the blood viscosity μ on the basis of the blood viscosity distribution DV, as one of blood state index values X1 for evaluating the blood state. Where the blood flow velocity distribution DS is a three-dimensional velocity vector distribution, the blood viscosity distribution DV is calculated according to the Navier-Stokes equations which are three-dimensional.

[Equation 2]

$$\frac{\partial u}{\partial t} + u\frac{\partial u}{\partial x} + v\frac{\partial u}{\partial y} = -\frac{1}{\rho}\frac{\partial p}{\partial x} + v\left(\frac{\partial^2 u}{\partial x^2} + \frac{\partial^2 u}{\partial y^2}\right) \quad (2)$$

[Equation 3]

$$\frac{\partial v}{\partial t} + u\frac{\partial v}{\partial x} + v\frac{\partial v}{\partial y} = -\frac{1}{\rho}\frac{\partial p}{\partial v} + v\left(\frac{\partial^2 v}{\partial x^2} + \frac{\partial^2 v}{\partial y^2}\right) \quad (3)$$

[Equation 4]

$$v = \frac{\mu}{\rho} \quad (4)$$

[Equation 5]

$$v = \frac{\frac{\partial \xi}{\partial t} + u\frac{\partial \xi}{\partial x} + v\frac{\partial \xi}{\partial y}}{\frac{\partial^2 \xi}{\partial x^2} + \frac{\partial^2 \xi}{\partial y^2}} \quad (5)$$

[Equation 6]

$$\xi = \frac{\partial u}{\partial y} - \frac{\partial v}{\partial x} \quad (6)$$

In the above Equations (2) and (3), the reference characters "x", "y", "u" and "v" are the same as those in the above Equation (1), and "t", "p", "ρ" and "v" respectively represent: time; pressure; density of the blood; and kinematic viscosity (coefficient of kinematic viscosity). Where the blood has the viscosity (coefficient of viscosity) μ, the kinematic viscosity v is calculated according to the above Equation (4). Alternatively, the kinematic viscosity v can be obtained according to the above Equation (5) which is derived by deleting the term of the pressure "p" included in the above Equations (2) and (3), by differentiation. In the Equation (5), "ξ" represents the vorticity, which is calculated according to the above Equation (6) and is defined by the velocity vector component only, as is apparent from this Equation (6).

Figure 9:
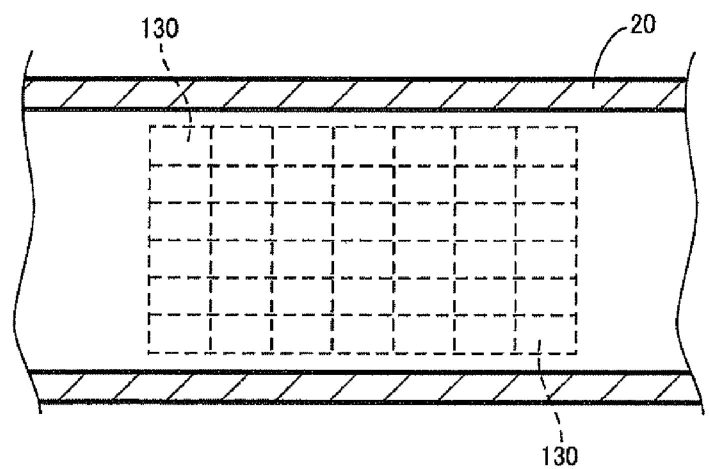
FIG. 9 is a view indicating an example of virtual division of a space within the blood vessel the blood flow velocity distribution of which is measured with the ultrasonic wave generated from the ultrasonic probe of FIG. 2, wherein the space is divided into a plurality of smaller sub-regions.

When the blood viscosity distribution calculating means 82 calculates the blood viscosity distribution DV on the basis of the blood flow velocity distribution DS, the blood is presumed to be incompressible, and the space within the blood vessel 20 is virtually divided into a plurality of smaller sub-regions 130, as shown in FIG. 9. The blood viscosity distribution calculating means 82 applies the above-described Navier-Stokes equations to each of the sub-regions 130 on the assumption that the density ρ and the viscosity μ of the blood are constant within each of the sub-regions 130, and combines together the values of the blood viscosity μ calculated for the respective sub-regions 130, to calculate the blood viscosity distribution DV.

The blood shear rate distribution calculating means 84 is configured to calculate the shear rate distribution DSR of the blood within the blood vessel 20 under measurement, on the basis of the blood flow velocity distribution DS measured by the blood flow velocity distribution measuring means 80. Described more specifically, the blood shear rate distribution calculating means 84 obtains a two-dimensional shear rate tensor on the basis of the blood flow velocity distribution DS (two-dimensional velocity vector distribution), and determines, by approximation, the normal direction of the blood vessel 20 to be a direction normal to a line of the blood flow a direction of tangency of which is parallel to the direction of the two-dimensional velocity vector. The blood shear rate distribution calculating means 84 obtains a shear component $e_{xy0}$ by rotatory coordinate conversion (indicated by arrow-headed lines AR1 in FIG. 7) of the above-described two-dimensional shear rate component with respect to the normal direction of the blood vessel 20 determined by approximation as described above, and extracts the shear component $e_{xy0}$ as the blood shear rate SR, to calculate the blood shear rate distribution DSR. A solid line L03 in the illustrative view of FIG. 10 indicates an example of the instantaneous blood shear rate distribution DSR. For quantitative determination of the shear rate of the blood (blood shear rate) SR, the shear rate distribution calculating means 84 calculates an average value of the blood shear rate SR on the basis of the blood shear rate distribution DSR, as one of the above-described blood state index values X1. It is noted that the above-described shear component $e_{xy0}$ is represented by the following Equation (7), which is stored in the blood shear rate distribution calculating means 84. Where the blood flow velocity distribution DS is a three-dimensional velocity vector distribution, the blood shear rate distribution DSR is calculated according to the above-described shear rate tensor which is three-dimensional. The values $x_0$, $y_0$, $u_0$ and $v_0$ in the following Equation (7) are obtained by rotatory coordinate conversion (indicated by the arrow-headed lines AR1 in FIG. 7) of the values x, y, u and v in the above Equation (1), and the $y_0$ axis coincides with the direction normal to the blood vessel wall, and the $x_0$ axis coincides with the longitudinal direction of the blood vessel 20, as indicated in FIGS. 2 and 7. Further, the y axis coincides with the direction of the ultrasonic wave beam axis, and the x axis coincides with the direction perpendicular to the ultrasonic wave beam axis. The character "$u_0$" represents the velocity component in the $x_0$ direction, and the reference character "$v_0$" represents the velocity component in the $y_0$ direction.

[Equation 7]

$$e_{xy0} = \frac{1}{2}\left(\frac{\partial u_0}{\partial y_0} + \frac{\partial v_0}{\partial x_0}\right) \quad (7)$$

When the blood shear rate distribution calculating means 84 calculates the blood shear rate distribution DSR on the basis of the blood flow velocity distribution DS, the space within the blood vessel 20 is virtually divided into the plurality of smaller sub-regions 130, as shown in FIG. 9, as in the calculation of the blood viscosity distribution DV, and applies the above-described Equation (7) to each of the sub-regions 130, and combines together the values of the blood viscosity μ calculated for the respective sub-regions 130, to calculate the shear component $e_{xy0}$ as the blood shear rate SR for each sub-region 130. The blood shear rate distribution calculating means 84 calculates the blood shear rate distribution DSR by combining the values of the blood shear rate SR ($e_{xy0}$) calculated for the respective sub-regions 130.

The shear stress distribution calculating means 86 calculates the shear stress distribution of the blood (blood shear stress distribution) DSS on the basis of the above-described blood viscosity distribution DV and blood shear rate distribution DSR, and according to the Newton's law of viscosity which is represented by the following Equation (8) and which is stored in memory. For calculating the blood shear stress distribution DSS, the above-described blood viscosity distribution DV may be replaced by the average value of the above-described blood viscosity μ. A solid line L04 in the illustrative view of FIG. 11 indicates an example of the instantaneous blood shear stress distribution DSS. For quantitative determination of the shear stress of the blood (blood shear stress) SS, the shear stress distribution calculating means 86 calculates an average value of the blood shear stress SS on the basis of the blood shear stress distribution DSS, as one of the above-described blood state index values X1.

[Equation 8]

$$(\text{Shear stress})=(\text{Viscosity})\times(\text{Shear rate}) \quad (8)$$

Figure 10:
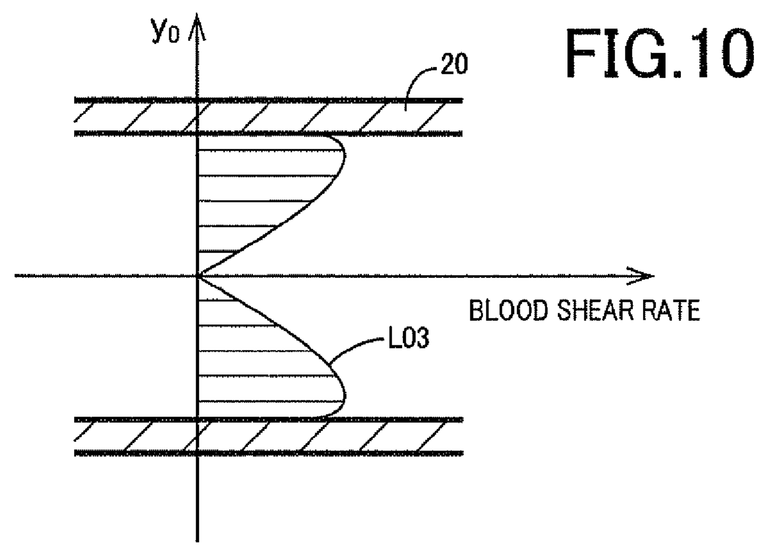
FIG. 10 is an illustrative view indicating a blood shear rate distribution calculated by shear rate distribution calculating means provided in the blood vessel function inspecting apparatus of FIG. 5.
Figure 11:
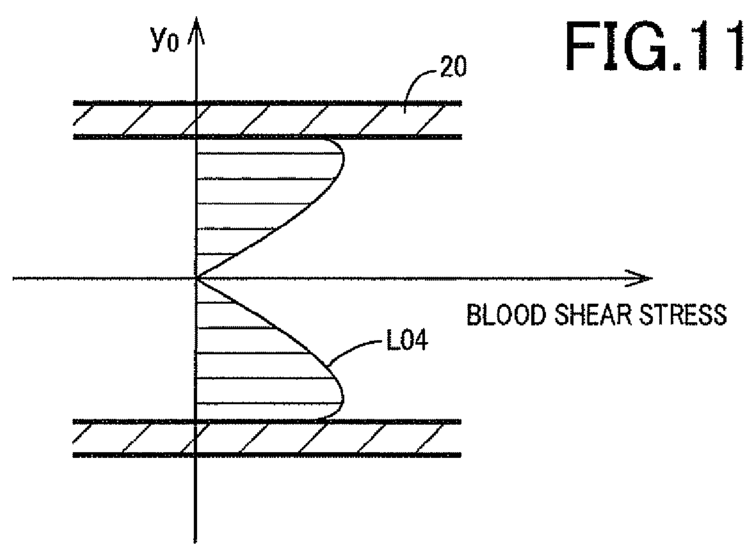
FIG. 11 is an illustrative view indicating a blood shear stress distribution calculated by shear stress distribution calculating means provided in the blood vessel function inspecting apparatus of FIG. 5.

When the shear stress distribution calculating means 86 calculates the blood shear stress distribution DSS on the basis of the above-described blood viscosity distribution DV and blood shear rate distribution DSR, the space within the blood vessel 20 is virtually divided into the plurality of smaller sub-regions 130, as shown in FIG. 9, as in the calculation of the blood viscosity distribution DV and blood shear rate distribution DSR, and the shear stress distribution calculating means 86 calculates the blood shear stress SS for each of the sub-regions 130, by multiplying the blood viscosity μ calculated for each sub-region 130 by the blood shear rate SR calculated for each sub-region 130 according to equation of the Newton's law of the viscosity. The blood shear stress distribution calculating means 86 then calculates the blood shear stress distribution DSS by combining together the values of the blood shear stress SS calculated for the respective sub-regions 130. FIGS. 6, 8, 10 and 11 referred to above are illustrative views, which are not necessarily coincident with the views of the actual distributions. The blood shear rate distribution DSR indicated in FIGS. 10 and 11 is based on absolute coordinate values obtained as a result of processing of the blood flow velocity distribution DS according to a difference equation.

The blood state index value calculating means 88 is configured to calculate the above-described blood state index values X1 on the basis of the blood viscosity distribution DV and the blood shear rate distribution DSR. To this end, the blood state index value calculating means 88 is provided with first blood state index value calculating means 90 and second blood state index value calculating means 92.

The first blood state index value calculating means 90 stores therein a plurality of predetermined points within the blood vessel 20 under measurement, that is, a plurality of sampling points, for extracting a plurality of sets of values of the blood viscosity μ and the blood shear rate SR from the calculated blood viscosity distribution DV and blood shear rate distribution DSR. The plurality of sampling points are arbitrarily scattered within an area of the blood vessel 20 in which the above-described blood viscosity distribution DV and blood shear rate distribution DSR are calculated. The first blood state index value calculating means 90 extracts the values of the blood viscosity μ and blood shear rate SR at the plurality of sampling points, from the blood viscosity distribution DV and blood shear rate distribution DSR. The values of the blood viscosity μ and blood shear rate SR of each set are extracted at the corresponding one of the above-described sampling points in the space within the blood vessel 20. Where the blood viscosity distribution DV and blood shear rate distribution DSR are extracted chronologically continuously rather than instantaneously, the values of the blood viscosity μ and blood shear rate SR of each set are extracted at the same timing.

Figure 12:
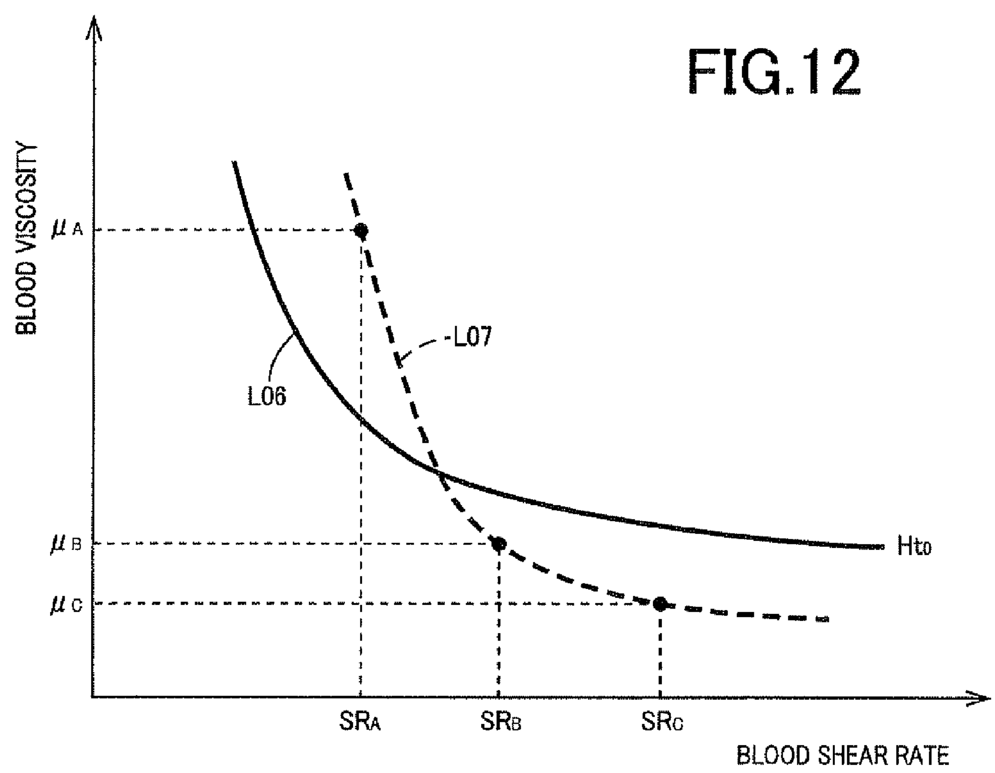
FIG. 12 is a view indicating examples of a relationship between a blood viscosity and a blood shear rate extracted from the blood viscosity distribution and the blood shear rate distribution in the blood vessel function inspecting apparatus of FIG. 5.

FIG. 12 is the view indicating examples of a relationship between the blood viscosity μ and the blood shear rate SR extracted from the blood viscosity distribution DV and the blood shear rate distribution DSR. In the examples of FIG. 12, three sets of values of the blood viscosity μ and blood shear rate SR are extracted. A solid line L06 indicates the comparative example of the relationship between the blood viscosity μ and the blood shear rate SR of a healthy person having a normal hematocrit value $Ht_0$. Described more specifically, the relationship between the blood viscosity μ and the blood shear rate SR indicated by this solid line L06 is represented by the following Equation (9). In the following Equation (9), "A" and "α" represent constants determined by the hematocrit value Ht used as a parameter. "$Ht_0$" in FIG. 12 represents the hematocrit value Ht of the healthy person, namely, the normal value of the hematocrit value Ht (hereinafter referred to as "reference hematocrit value $Ht_0$"), which is a predetermined value within a range of 40%-50% for the male persons, and a predetermined value within a range of 35%-45% for the female persons.

[Equation 9]

$$\mu = A \cdot e^{-\alpha \cdot SR} \quad (9)$$

In the examples of FIG. 12, the blood viscosity μ and the blood shear rate SR are extracted at three sampling points. At the first sampling point $P_A$, a blood viscosity value $\mu_A$ and a blood shear rate value $SR_A$ are extracted. At the second sampling point $P_B$, a blood viscosity value $\mu_B$ and a blood shear rate value $SR_B$ are extracted. At the third sampling point $P_C$, a blood viscosity value $\mu_C$ and a blood shear rate value $SR_C$ are extracted. The blood viscosity values $\mu_A$, $\mu_B$, $\mu_C$ and the blood shear rate values $SR_A$, $SR_B$, $SR_C$ represent a relationship as indicated by a broken line L07 in FIG. 12. The relationship (indicated by the broken line L07) between the blood viscosity $\mu$ and the blood shear rate SR in FIG. 12 changes depending upon the blood viscosity distribution DV and the blood shear rate distribution DSR.

Figure 13:
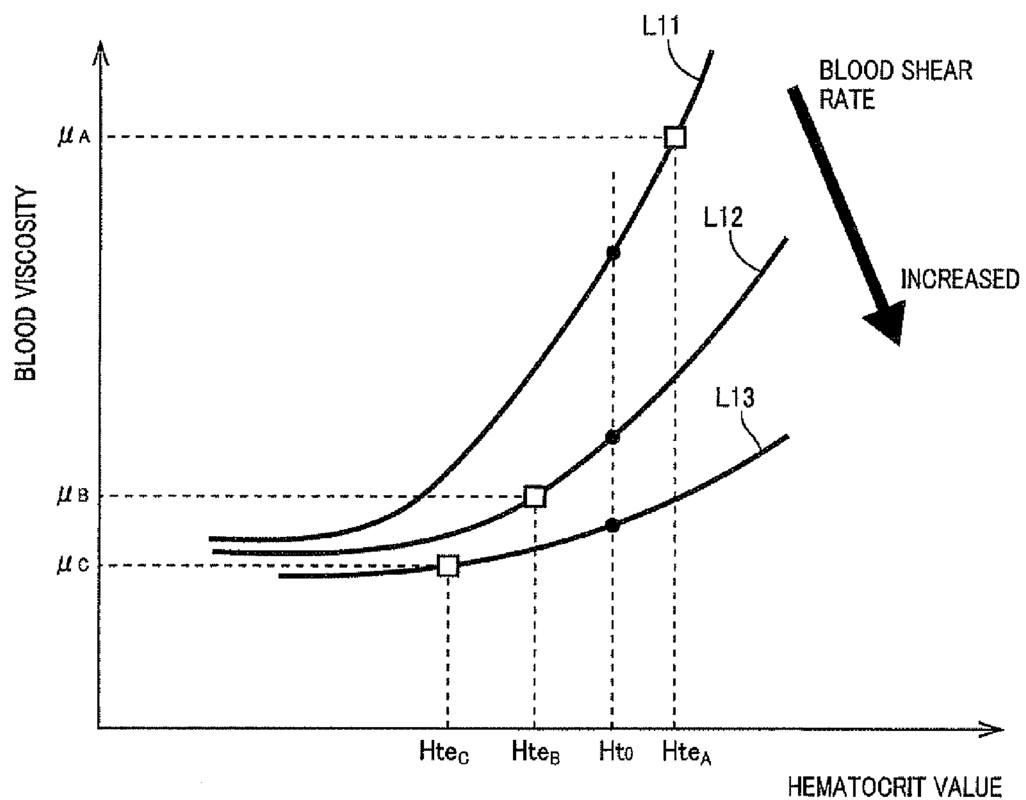
FIG. 13 is a view indicating reference relationships between a hematocrit value and the blood viscosity, which are preliminarily stored in the blood vessel function inspecting apparatus of FIG. 5 and which are indicated in relation to the blood shear rate as a parameter.

FIG. 13 is the view indicating reference relationships between the hematocrit value Ht and the blood viscosity $\mu$, which are indicated in relation to the blood shear rate SR used as a parameter, predetermined on the assumption that the blood is normal. The blood viscosity $\mu$ may be influenced by factors such as plasma protein concentration in addition to the hematocrit value Ht. The normal blood is interpreted to mean that the blood has a normal state in which the blood viscosity $\mu$ is not influenced or not substantially influenced by factors other than the hematocrit value Ht. The reference relationships described are relationships of the healthy person whose blood has the above-described reference hematocrit value $Ht_0$, between the hematocrit value Ht and the blood viscosity $\mu$, wherein the hematocrit value Ht varies with respect to the reference hematocrit value $Ht_0$. The above-described reference relationships are predetermined and stored in the first blood state index value calculating means 90.

The first blood state index value calculating means 90 obtains an estimated hematocrit value Hte for each of the above-indicated plurality of sampling points, on the basis of the blood viscosity $\mu$ and the blood shear rate SR at the sampling points, and according to the above-described referenced relationships indicated in FIG. 13. This operation of the first blood state index value calculating means 90 will be described by reference to FIG. 13, taking an example in which a set of the blood viscosity value $\mu_A$ and blood shear rate value $SR_A$, a set of the blood viscosity value $\mu_B$ and blood shear rate value $SR_B$, and a set of the blood viscosity value $\mu_C$ and blood shear rate value $SR_C$ are extracted at the respective three sampling points $P_A$, $P_B$ and $P_C$, as in the case of FIG. 12.

As indicated in FIG. 13, the first blood state index value calculating means 90 obtains an estimated hematocrit value $Hte_A$ on the basis of the blood viscosity value $\mu_A$ and according to the above-described reference relationship L11 where the blood shear rate SR is equal to $SR_A$, obtains an estimated hematocrit value $Hte_B$ on the basis of the blood viscosity value $\mu_B$ and according to the above-described reference relationship L12 where the blood shear rate SR is equal to $SR_B$, and obtains an estimated hematocrit value $Hte_C$ on the basis of the blood viscosity value $\mu_C$ and according to the above-described reference relationship L13 where the blood shear rate SR is equal to $SR_C$. The above-described reference relationships indicated in FIG. 13 are based on the assumption that the blood has the normal state, and the bloods having the same state actually have the same hematocrit value Ht. Therefore, the hematocrit value Ht of the healthy person having the normal blood state, which is obtained according to the above-described reference relationships, should be equal to the reference hematocrit value $Ht_0$ at any blood shear rate SR. Namely, the estimated hematocrit values $Hte_A$, $Hte_B$ and $Hte_C$ which deviate from the reference hematocrit value $Ht_0$ or which have a difference with respect to each other indicate an abnormality of the blood state in FIG. 13. In view of this fact, the first blood state index value calculating means 90 calculates, as one of the above-described blood state index values X1, each of: an average value of the estimated hematocrit values $Hte_A$, $Hte_B$ and $Hte_C$ obtained according to the above-described reference relationships of FIG. 13; a difference of this average value with respect to the reference hematocrit value $Ht_0$; and an amount of difference of the estimated hematocrit values $Hte_A$, $Hte_B$ and $Hte_C$ with respect to each other, for example, an amount of the difference between the maximum value ($Hte_A$) and the minimum value ($Hte_C$). The average value of the above-described estimated hematocrit values $Hte_A$, $Hte_B$ and $Hte_C$ is considered to be an estimated value of the hematocrit value Ht which has a certain degree of reliability. Further, the difference of the average value of the above-descried estimated hematocrit values $Hte_A$, $Hte_B$ and $Hte_C$ with respect to the reference hematocrit value $Ht_0$, and the amount of difference of the estimated hematocrit values $Hte_A$, $Hte_B$ and $Hte_C$ with respect to each other indicate a degree of abnormality of the blood state. The degree of reliability of the average value of the above-described estimated hematocrit values $Hte_A$, $Hte_B$ and $Hte_C$ is considered to increase with a decrease of the amount of difference of the estimated hematocrit values $Hte_A$, $Hte_B$ and $Hte_C$ with respect to each other.

After the first blood state index value calculating means 90 obtains the estimated hematocrit values $Hte_A$, $Hte_B$ and $Hte_C$ according to the above-described reference relationships of FIG. 13, the second blood state index value calculating means 92 transforms the above-descried reference relationships of FIG. 13 at the same ratio for all of the different blood shear rate values SR, to minimize the amount of difference of the estimated hematocrit values $Hte_A$, $Hte_B$ and $Hte_C$ at the above-described plurality of sampling points $P_A$, $P_B$ and $P_C$, for instance, an amount of the difference between the maximum and minimum values of the values $Hte_A$, $Hte_B$ and $Hte_C$. This aspect will be described by reference to FIG. 14.

Figure 14:
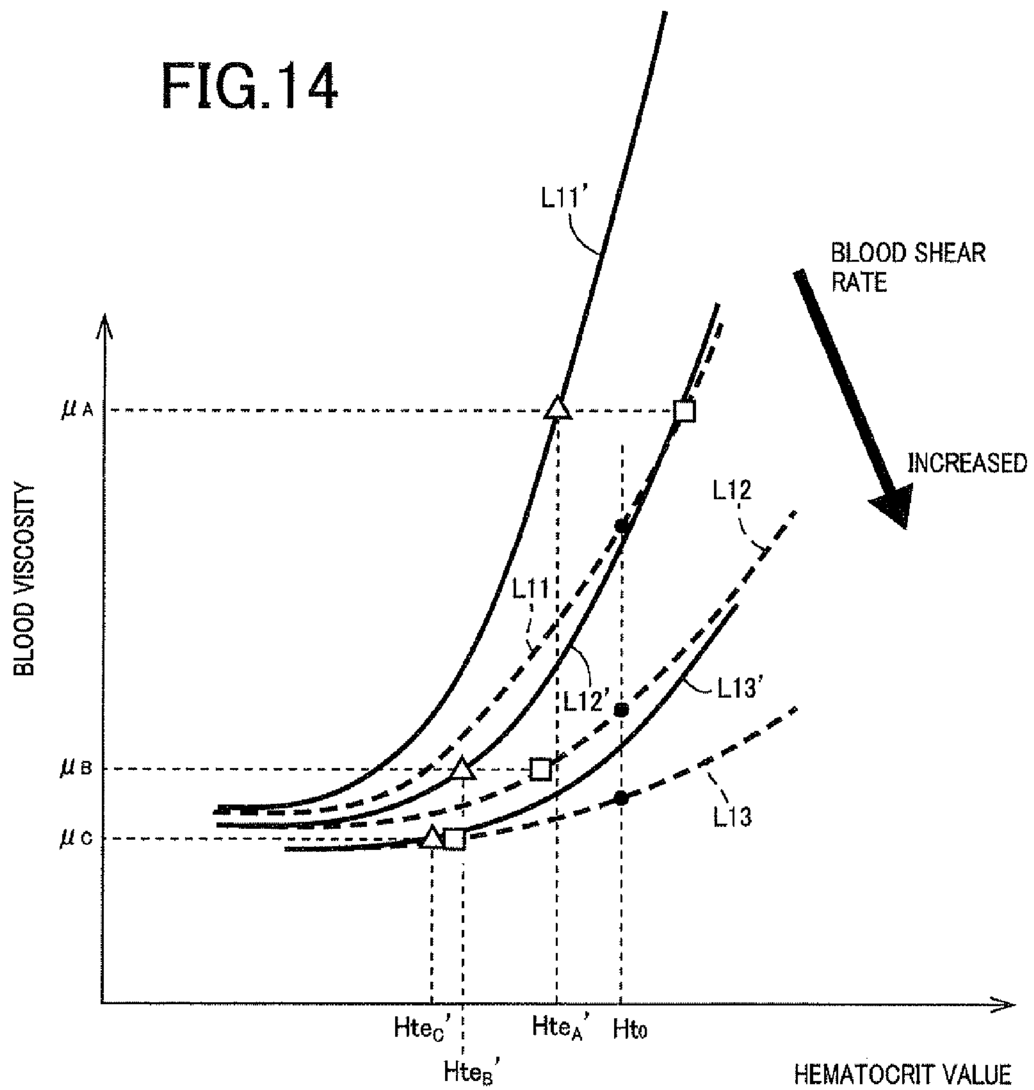
FIG. 14 is a view for explaining transformation of the above-described reference relationships at the same ratio for all values of the blood shear rate.

FIG. 14 is the view for explaining the transformation of the above-described reference relationships in FIG. 13 at the same ratio for all different values of the blood shear rate SR. In FIG. 14, broken lines L11, L12 and L13 represent the above-described reference relationships of FIG. 13 before the transformation. Namely, the broken lines L11, L12 and L13 of FIG. 14 are identical with the curves of the solid lines L11, L12 and L13 of FIG. 13, respectively. Solid lines L11', L12' and L13' in FIG. 14 are curves obtained by transforming the respective broken lines L11, L12 and L13, and $Hte_A'$, $Hte_B'$ and $Hte_C'$ in FIG. 14 are respectively the estimated hematocrit values obtained according to the transformed reference relationships L11', L12' and L13'.

The second blood state index value calculating means 92 transforms the above-described reference relationships L11, L12 and L13 at the same ratio for all of the different values of the blood shear rate SR, by using the same coefficient $C_E$ to change relationship equations defining the respective reference relationships L11, L12 and L13 corresponding to the respective different values of the blood shear rate SR, for example. Described more specifically, where the relationship equations defining the above-described reference relationships L11, L12 and L13 are respectively represented by the following Equations (10), (11) and (12) wherein the common coefficient $C_E$ is equal to "1", the second blood state index value calculating means 92 transforms the above-described reference relationships L11, L12 and L13 at the same ratio, by changing the coefficient $C_E$ to a value larger than "1".

[Equation 10]

$$\mu = C_E \cdot f_1(Ht) \quad (10)$$

[Equation 11]

$$\mu = C_E \cdot f_2(Ht) \quad (11)$$

[Equation 12]

$$\mu = C_E \cdot f_3(Ht) \quad (12)$$

Then, the second blood state index value calculating means 92 obtains the estimated hematocrit value $Hte_A'$ on the basis of the blood viscosity $\mu_A$ and according to the transformed reference relationship L11', obtains the estimated hematocrit value $Hte_B'$ on the basis of the blood viscosity $\mu_B$ and according to the transformed reference relationship L12', and obtains the estimated hematocrit value $Hte_C'$ on the basis of the blood viscosity $\mu_C$ and according to the transformed reference relationship L13'. The second blood state index value calculating means 92 repeatedly transforms the reference relationships and obtains the post-transformation estimated hematocfrit values $Hte_A'$, $Hte_B'$, $Hte_C'$ (referred to as "estimated hematocrit values Hte'", unless otherwise specified), so as to minimize the amount of difference of the estimated hematocrit values $Hte_A'$, $Hte_B'$, $Hte_C'$ with respect to each other. The second blood state index value calculating means 92 stores the estimated hematocrit values $Hte_A'$, $Hte_B'$, $Hte_C'$ at the time the amount of difference of which has been minimized, as post-convergence estimated hematocrit values $Hte_{AE}$, $Hte_{BE}$, $Hte_{CE}$ (referred to as "post-convergence estimated hematocrit values $Hte_E$", unless otherwise specified) in relation to the above-described plurality of sampling points $P_A$, $P_B$, $P_C$, respectively, and further stores the coefficient $C_E$ at the time the above-described amount of difference has been minimized, as a post-convergence coefficient $C1_E$.

Then, the second blood state index value calculating means 92 calculates, as the above-described blood state index value X1, a value relating to the amount of the difference (minimized amount of difference) $RHte_E$ of the post-convergence estimated hematocrit values $Hte_{AE}$, $Hte_{BE}$, $Hte_{CE}$. Described more specifically, the above-indicated value relating to the minimized amount of the difference $RHte_E$ may be selected, for instance, from (i) the above-indicated minimized amount of the difference $RHte_E$ per se as represented by the minimum and maximum values defining the difference $RHte_E$, for example, (ii) an average of the post-convergence estimated hematocrit values $Hte_{AE}$, $Hte_{BE}$, $Hte_{CE}$ at the respective sampling points $P_A$, $P_B$, $P_C$ described above, (iii) an average $Hte_{AVGE}$ of differences of the post-convergence estimated hematocrit values $Hte_{AE}$, $Hte_{BE}$, $Hte_{CE}$ with respect to the reference hematocrit value $Ht_0$, and (iv) the post-convergence coefficient $C1_E$. Accordingly, the second blood state index value calculating means 92 calculates a selected one or all of the values indicated above at (i) through (iv), as the above-described blood state index value or values X1. The average of the above-described post-convergence estimated hematocrit values $Hte_{AE}$, $Hte_{BE}$, $Hte_{CE}$ is also effective as the estimated value of the hematocrit value Ht having a certain degree of reliability, and the above-described degree of reliability of the average of the post-convergence estimated hematocrit values $Hte_{AE}$, $Hte_{BE}$, $Hte_{CE}$ is considered to increase with a decrease of the minimized amount of the difference $RHte_E$. Further, the average $Hte_{AVGE}$ of the differences of the post-convergence estimated hematocrit values $Hte_{AE}$, $Hte_{BE}$, $Hte_{CE}$ with respect to the reference hematocrit value $Ht_0$, is considered to indicate a degree of abnormality of the blood as evaluated from the hematocrit value Ht, and the post-convergence coefficient $C1_E$ is considered to indicate the degree of abnormality of the blood as seen from the factors other than the hematocrit value Ht, such as the plasma protein concentration, which influence the blood viscosity μ. For example, the degree of abnormality of the blood is determined to increase with an increase of the post-convergence coefficient $C1_E$.

The blood state abnormality detecting means 94 is configured to determines the abnormality of the blood state on the basis of the blood state index values X1 calculated as described above. Described more specifically, the blood state abnormality detecting means 94 determines that the blood state is abnormal, if the average $Hte_{AVGE}$ of the differences of the post-convergence estimated hematocrit values $Hte_{AE}$, $Hte_{BE}$, $Hte_{CE}$ with respect to the reference hematocrit value $Ht_0$ (hereinafter referred to as "remaining-difference average $Hte_{AVGE}$") is larger than a predetermined threshold value $XHt_{AVG}$. This threshold value $XHt_{AVG}$ for the remaining-difference average $Hte_{AVGE}$ is obtained by experimentation for determining the abnormality of the blood state, and stored in the blood state abnormality detecting means 94. For instance, the abnormal states of the blood may include a state of the blood in which the plasma protein concentration is outside a predetermined normal range, and a state of the blood in which the hematocrit value Ht is outside a predetermined normal range. Preferably, the absolute value of the remaining-difference average $Hea_{ve}$ is used when it is compared with the above-described threshold value $Heav_y$.

The blood vessel diameter measuring means 96 is configured to synthesize an image on the basis of the scattered (reflected) ultrasonic waves received by the first short-axis ultrasonic detector array A of the ultrasonic probe 24, and to measure the blood vessel lumen diameter $d_1$ on the basis of the synthesized image. In particular, the blood vessel diameter measuring means 96 chronologically continuously measures the blood vessel lumen diameter $d_1$, which changes after the blood vessel releasing from the blood flow obstruction, as indicated in FIG. 4. Where the blood flow velocity distribution measuring means 80 measures the blood flow velocity distribution DS after the blood vessel releasing from the blood flow obstruction, the blood vessel diameter measuring means 96 may measure the blood vessel lumen diameter $d_1$ concurrently with the measurement of the blood flow velocity distribution DS. The blood vessel diameter measuring means 96 calculates and measures a ratio of the diameter change of the blood vessel 20 after its releasing from the blood flow obstruction, more specifically, the dilatation ratio R of the above-described blood vessel lumen diameter $d_1$, on the basis of a result of the measurement of the blood vessel lumen diameter $d_1$ after the above-described blood vessel releasing.

The blood vessel dilatation index value calculating means 98 is configured to calculate a maximum value $R_{MAX}$ (%) ($=100\times(d_{MAX}-d_a)/d_a$) of the diameter change ratio (dilatation ratio R) of the blood vessel 20 calculated by the blood vessel diameter measuring means 96 after the blood vessel releasing from the blood flow obstruction, as one of blood vessel dilation index values X2 used for evaluating the blood vessel dilatation function.

Where the blood flow velocity distribution DS is measured concurrently with the measurement of the above-described blood vessel lumen diameter $d_1$ after the blood vessel releasing from the blood flow obstruction, the blood vessel dilatation index value calculating means 98 calculates a maximum value $SS_{MAX}$ of the blood shear stress SS (maximum blood shear stress value $SS_{MAX}$) within the blood shear stress distribution DSS calculated by the shear stress distribution calculating means 86, on the basis of the measured blood flow velocity distribution DS. Then, the blood vessel dilatation index value calculating means 98 calculates, as one of the above-described blood vessel dilatation index values X2, a ratio between the maximum blood shear stress value $SS_{MAX}$ and the maximum value $R_{MAX}$ of the diameter change ratio of the blood vessel 20 (maximum blood vessel diameter change ratio value $R_{MAX}$) after the above-described blood vessel releasing. While either one of the maximum blood shear stress value $SS_{MAX}$ and the maximum blood vessel diameter change ratio value $R_{MAX}$ may be the denominator of the ratio, the above-described maximum blood shear stress value $SS_{MAX}$ is selected, for example, as the denominator to calculate the above-described blood vessel dilatation index value X2. The above-described maximum blood shear stress value $SS_{MAX}$ relating to the above-described blood vessel dilation index value X2 may be a maximum value of the blood shear stress SS within the blood shear stress distribution DSS when the blood flow velocity after the above-described blood vessel releasing is highest, for instance, or conversely, a maximum value of the blood shear stress SS within the blood shear stress distribution DSS when the blood flow velocity after the above-described blood vessel releasing is lowest. The maximum blood shear stress value $SS_{MAX}$ may be a maximum value of the average of the blood shear stress SS which varies after the above-described blood vessel releasing. In summary, the above-described maximum blood shear stress value $SS_{MAX}$ must be consistently obtained in a predetermined condition.

The blood vessel dilatation function abnormality detecting means 100 is configured to make a determination regarding the abnormality of the blood vessel dilatation function on the basis of the calculated blood vessel dilatation index value X2. Described more specifically, the blood vessel dilatation function abnormality detecting means 100 determines that the blood vessel dilatation function is abnormal, if the above-described blood vessel dilatation index value X2 which is the ratio between the above-described maximum blood shear stress value $SS_{MAX}$ and the above-described maximum blood vessel diameter change ratio value $R_{MAX}$ after the blood vessel releasing is outside a predetermined normal range RX2. The blood vessel dilatation function abnormality detecting means 100 employs the ratio between the above-described maximum blood shear stress value $SS_{MAX}$ and the above-described maximum blood vessel diameter change ratio value $R_{MAX}$ after the blood vessel releasing, as the blood vessel dilatation index value X2 to be compared with the above-described normal range RX2. This normal range RX2 is stored in the blood vessel dilatation abnormality detecting means 100, for making the determination as to whether the blood vessel dilatation function is abnormal, on the basis of the above-described blood vessel dilatation index value X2. The above-described blood vessel dilation index value X2 within the normal range RX2 indicates that the blood vessel is in a predetermined normal state of the dilatation function. When the blood vessel dilatation function abnormality detecting means 100 determines that the above-described blood vessel dilatation index value X2 is outside the above-described normal range RX2, that is, determines that the blood vessel dilatation function is abnormal, the blood vessel dilatation function abnormality detecting means 100 may calculate an amount of deviation of the blood vessel dilatation index value X2 from the upper and lower limits of the normal range RX2, namely, an amount of a difference (an amount of an error) of the blood vessel dilatation index value X2 (the ratio between the above-described maximum blood shear stress value $SS_{MAX}$ and the above-described maximum blood vessel diameter change ratio value $R_{MAX}$ after the blood vessel releasing) with respect to the upper and lower limits of the normal range RX2, and may use the calculated amount of deviation as an updated one of the above-described blood vessel dilatation index values X2, which can be used as an index value indicative of the degree of abnormality of the above-described blood vessel dilatation function.

The display control means 102 is configured to display, on the monitoring image display device 30, the measured or calculated blood flow velocity distribution DS, blood viscosity distribution DS, blood shear rate distribution DSR, blood shear stress distribution DSS, blood state index values X1, and blood vessel dilatation index values X2. The display control means 102 also displays, on the monitoring image display device 30, the results of determinations made by the blood state abnormality detecting means 94 and the blood vessel dilatation function abnormality detecting means 100.

The display control means 102 is further configured to display, on the monitoring image display device 30, the transverse cross sectional image (short-axis image) and longitudinal cross sectional image (long-axis image) of the blood vessel 20 below the skin 18, which are generated on the basis of the reflected waves of the ultrasonic wave beam received by the echo receiving means 72.

Figure 15:
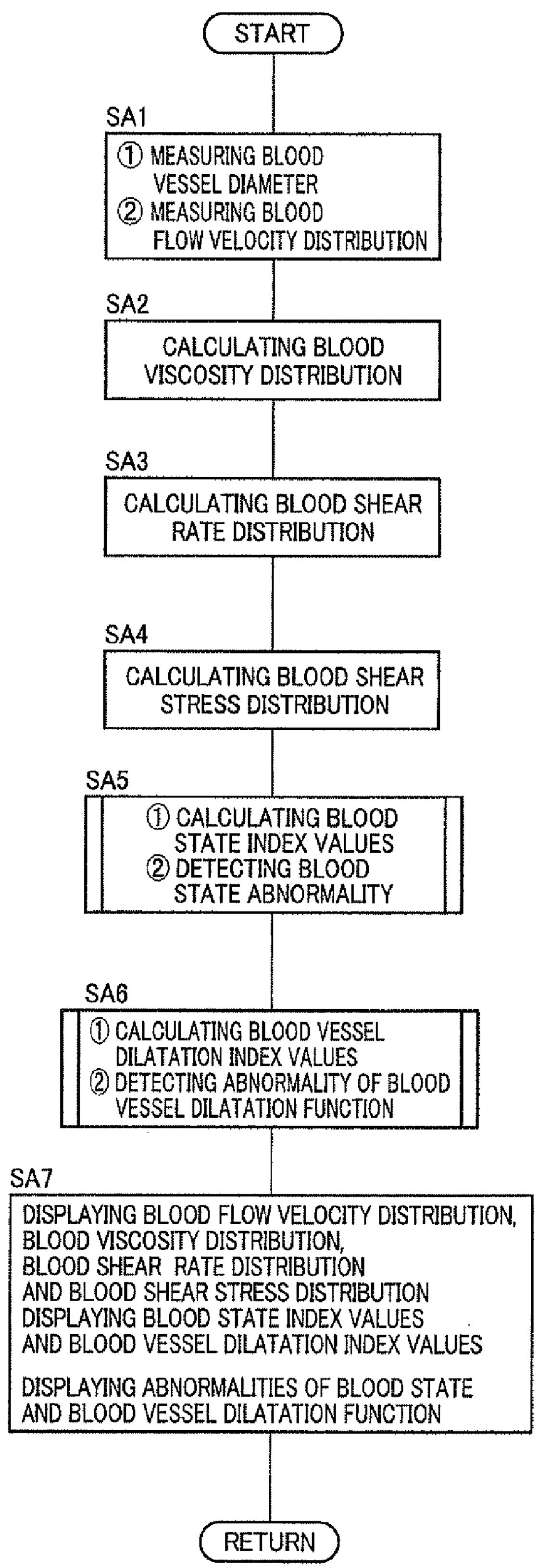
FIG. 15 is a flow chart illustrating a major control operation of the blood vessel function inspecting apparatus (electronic control device) of FIG. 5, namely, a control operation performed to evaluate the blood state and the blood vessel dilatation function in a non-invasion manner.

FIG. 15 is the flow chart illustrating a major control operation of the blood vessel function inspecting apparatus 22 (electronic control device 28), namely, a control operation to performed to evaluate the blood state and the blood vessel dilatation function in a non-invasion manner.

Initially, step SA1 (hereinafter "step" being omitted) corresponding to the blood flow velocity distribution measuring means 80 and the blood vessel diameter measuring means 96 is implemented to measure the blood flow velocity distribution DS in the non-invasion manner, with the ultrasonic waves which are irradiated from the ultrasonic probe 24 and which are percutaneously incident upon the blood vessel 20 within the live body 14. For instance, the blood flow velocity distribution DS is chronologically continuously measured after the releasing of the blood vessel 20 from the blood flow obstruction. Further, the diameter change ratio (dilatation ratio R) of the blood vessel 20 after its releasing from the blood flow obstruction is measured by chronologically continuous measurement of the blood vessel lumen diameter $d_1$ after the blood vessel releasing, concurrently with the measurement of the blood flow velocity distribution DS. It is noted that the echo transmitted and received in the direction of the $y_0$ axis indicated in FIG. 7 is used to measure the blood vessel lumen diameter $d_1$, and the echo transmitted and received in the direction of the y axis indicated in FIG. 7 is used to measure the blood flow velocity.

In SA2 corresponding to the blood viscosity distribution calculating means 82, the blood viscosity distribution DV is calculated on the basis of the blood flow velocity distribution DS measured in SA1.

In SA3 corresponding to the shear rate distribution calculating means 84, the blood shear rate distribution DSR is calculated on the basis of the blood flow velocity distribution DS measured in SA1.

In SA4 corresponding to the shear stress distribution calculating means 86, the blood shear stress distribution DSS is calculated on the basis of the blood viscosity distribution DV calculated in SA2 and the blood shear rate distribution DSR calculated in SA3, and according to the above-described Newton's law of viscosity (Equation (8)) stored in memory.

In SA5, the calculation of the above-described blood state index values X1 and the detection of an abnormality of the blood state are implemented. Described more specifically, a control operation according to the flow chart of FIG. 16 is performed in SA5.

Figure 16:
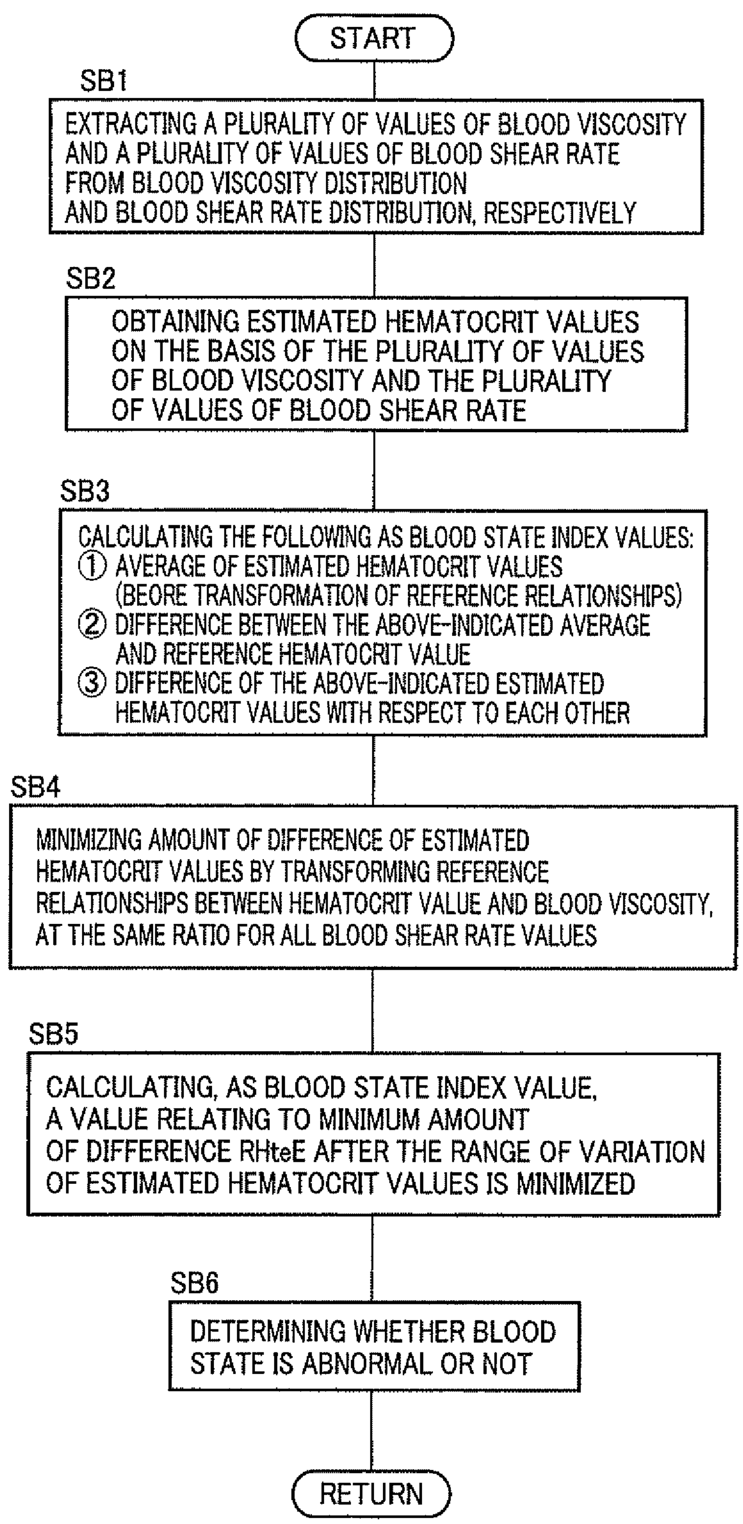
FIG. 16 is a flow chart illustrating a major control operation performed in SA5 of FIG. 15, namely, a control operation performed to calculate blood state index values and to detect an abnormality of the blood state.

FIG. 16 is the flow chart illustrating a major control operation performed in SA5 of FIG. 15, namely, the control operation performed to calculate the above-described blood state index values X1 and to detect an abnormality of the blood state.

In SB1 of FIG. 16, the values of the blood viscosity μ and blood shear rate SR at the respective sampling points (a plurality of points) are extracted from the above-described blood viscosity distribution DV and blood shear rate distribution DSR, respectively.

In SB2, the estimated hematocrit values Hte at the respective sampling points are obtained on the basis of the values of the blood viscosity μ and blood shear rate SR at the respective sampling points, and according to the above-described reference relationships. In the examples of FIG. 13, for instance, the estimated hematocrit values $Hte_A$, $Hte_B$ and $Hte_C$ at the respective sampling points $P_A$, $P_B$, $P_C$ are obtained on the basis of the blood viscosity values $\mu_A$, $\mu_B$, $\mu_C$, and blood shear rate values $SR_A$, $SR_B$, $SR_C$, at the respective sampling points $P_A$, $P_B$, $P_C$, and according to the reference relationships L11, L12, L13.

SB3 is implemented to calculate, as the above-described blood state index values X1: the average value of the estimated hematocrit values Hte obtained according to the above-described reference relationships (before transformation) represented by the respective solid lines L11, L12 and L13 in FIG. 13; the difference of this average value with respect to the reference hematocrit value $Ht_0$; and the amount of difference of the estimated hematocrit values Hte with respect to each other. In the examples of FIG. 13, the average value of the estimated hematocrit values $Hte_A$, $Hte_E$ and $Hte_C$ obtained according to the above-described reference relationships L11, L12 and L13, the difference of this average value with respect to the reference hematocrit value $Ht_0$; and the amount of difference of the estimated hematocrit values $Hte_A$, $Hte_B$ and $Hte_C$ with respect to each other are calculated as the above-described blood state index values X1. It will be understood that SB1, SB2 and SB3 correspond to the first blood state index value calculating means 90.

SB4 is implemented to transform the above-descried reference relationships at the same ratio for all of the different blood shear rate values SR, to minimize the amount of difference of the estimated hematocrit values Hte at the above-described sampling points (for instance, an amount of the difference between the maximum and minimum values). In the examples of FIGS. 13 and 14, the above-described reference relationships L11, L12 and L13 are transformed at the same ratio for all of the different values of the blood shear rate SR, by using the same coefficient $C_E$ to change the relationship equations defining the respective reference relationships L11, L12 and L13 corresponding to the respective different values of the blood shear rate SR, for example.

SB5 is implemented to calculate, as the above-described blood state index value X1, the value relating to the amount of the difference (minimized amount of difference) $RHte_E$ of the above-described post-convergence estimated hematocrit values $Hte_E$, after the amount of the difference of the above-described estimated hematocrit values Hte is minimized by the transformation of the above-described reference relationships. It will be understood that SB4 and SB5 correspond to the second blood state index value calculating means 92.

In SB6 corresponding to the blood state abnormality detecting means 94, the determination as to whether the blood state is abnormal or not is made on the basis of the calculated blood state index values X1. For instance, the determination that the blood state is abnormal is made if the above-described remaining-difference average $Hte_{AVGE}$ of the post-convergence estimated hematocrit values Hte obtained as one of the blood state index values X1 is larger than the threshold value $XHt_{AVG}$.

Referring back to FIG. 15, SA6 is implemented to calculate the above-described blood vessel dilatation index values X2 and detect an abnormality of the blood vessel dilatation function. Described more specifically, a control operation according to the flow chart of FIG. 17 is performed in SA6.

Figure 17:
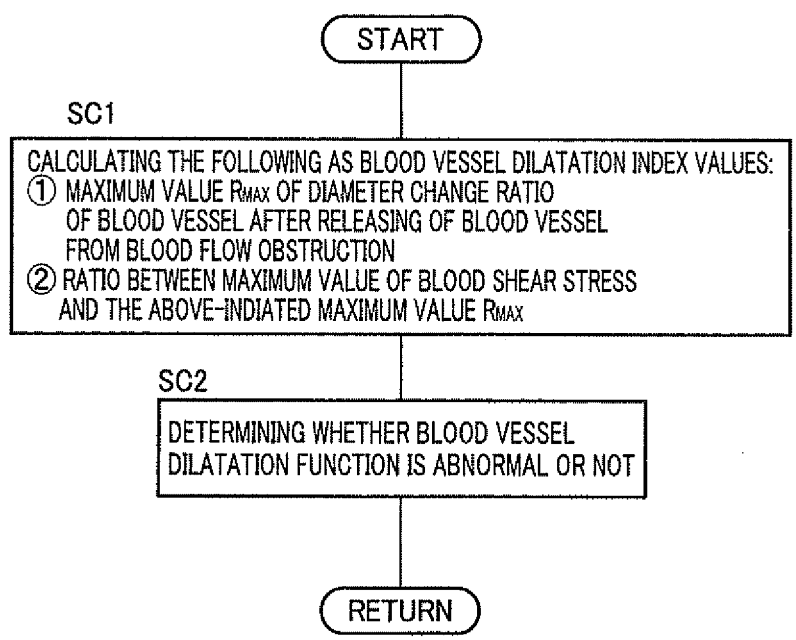
FIG. 17 is a flow chart illustrating a major control operation performed in SA6 of FIG. 15, namely, a control operation performed to calculate the blood vessel dilatation index values and to detect an abnormality of the blood vessel dilation function.

FIG. 17 is the flow chart illustrating a major control operation performed in SA6 of FIG. 15, namely, the control operation performed to calculate the above-described blood vessel dilatation index values X2 and to detect an abnormality of the blood vessel dilation function.

SC1 of FIG. 17 is implemented to calculate, as the above-described blood vessel dilatation index values X2, the above-described maximum blood vessel diameter change ratio value Rtx after the blood vessel releasing from the blood flow obstruction, and the ratio between the maximum blood shear stress value $SS_{MAX}$ within the blood shear stress distribution DSS and the maximum blood vessel diameter change ratio value $R_{MAX}$ after the blood vessel releasing. It will be understood that SC1 corresponds to the blood vessel dilatation index value calculating means 98.

In SC2, the determination as to whether the blood vessel dilatation function is abnormal or not is made on the basis of the calculated blood vessel dilatation index values X2. For instance, the determination that the blood vessel dilatation function is abnormal is made if the ratio between the above-described maximum blood shear stress value $SS_{MAX}$ and the above-described maximum blood vessel diameter change ratio value $R_{MAX}$ after the blood vessel releasing is outside the above-described normal range RX2. It will be understood that SC2 corresponds to the blood vessel dilatation function abnormality detecting means 100.

Referring back to FIG. 15, SA7 corresponding to the display control means 102 is implemented to display the measured or calculated blood flow velocity distribution DS, blood viscosity distribution DV, blood shear rate distribution DSR, blood shear stress distribution DSS, blood state index values X1, and blood vessel dilatation index values X2, on the monitoring image display device 30. The results of determination regarding the abnormalities of the blood state and the blood vessel dilatation function are also displayed on the monitoring image display device 30. The contents of information to be displayed on the monitoring image display device 30 may be printed on a recording medium such as sheets of paper, rather than, or in addition to, displayed on the monitoring image display device 30.

The present embodiment has the following advantages (A1) through (A8):

(A1) The present embodiment is configured such that the first blood state index value calculating means 90 obtains the estimated hematocrit values Hte at the above-described plurality of sampling points (plurality of points) within the blood viscosity distribution DV and the blood shear rate distribution DSR, on the basis of the values of the blood viscosity μ and the values of the blood shear rate SR at the plurality of sampling points, which are respectively extracted from the blood viscosity distribution DV and the blood shear rate distribution DSR, and according to the above-described reference relationships (represented by the solid lines L11, L12 and L13 in FIG. 13 by way of example) between the hematocrit value Ht and the blood viscosity μ, which reference relationships respectively correspond the predetermined different values of the blood shear rate SR as a parameter. Further, the second blood state index value calculating means 92 calculates, as the above-described blood state index value X1, the value relating to the amount of difference (minimized amount of difference) $RHte_E$ of the above-described post-convergence estimated hematocrit values $Hte_E$ with respect to each other when the amount of difference of the estimated hematocrit values Hte' at the above-described plurality of sampling points is minimized by transforming the above-described reference relationships at the same ratio for all of the values of the blood shear rate SR. Accordingly, it is possible to obtain the blood state index value X1 permitting the blood state evaluation, such as an index value equivalent to the hematocrit value Ht, in the non-invasion manner, to permit objective and easy evaluation of the blood state.

(A2) The present embodiment is further configured such that the value relating to the minimized amount of difference $RHte_E$ is the average of the estimated hematocrit values $Hte_E$ at the above-described plurality of sampling points. Accordingly, it is possible to obtain, in the non-invasion manner, an index value equivalent to the hematocrit value Ht conventionally used for clinical purposes.

(A3) The present embodiment is further configured such that the second blood state index value calculating means 92 calculates, as the above-described blood state index value X1, the average $Hte_{AVGE}$ (remaining-difference average) $Hte_{AVGE}$ of the differences of the post-convergence estimated hematocrit values $Hte_E$ at the above-described plurality of points with respect to the above-described reference hematocrit value $Ht_0$. The blood state abnormality detecting means 94 determines that the blood state is abnormal, if the above-described remaining-difference average $Hte_{AVGE}$ of the differences is larger than the above-described threshold value $XHt_{AVG}$. Accordingly, the determination as to whether the above-described blood state is abnormal or not can be made more easily than in the case where the above-described blood state abnormality detecting means 94 is not provided.

(A4) The present embodiment is further configured such that the second blood state index value calculating means 92 transforms the above-described reference relationships at the same ratio for all of the values of the blood shear rate SR, by changing relationship equations respectively defining the above-described reference relationships corresponding to the respective different values of the blood shear rate SR, with the same coefficient $C_E$, and determines, as the above-described blood state index value X1, the above-described post-convergence coefficient $C1_E$ which is the coefficient $C_E$ when the amount of difference of the above-described estimated hematocrit values Hte' at the above-described plurality of points is minimized. Accordingly, the blood state as seen from the factors other than the hematocrit value Ht, such as the plasma protein concentration, which influence the blood viscosity μ, can be evaluated on the basis of the above-described blood state index value X1 (post-convergence coefficient $C1_E$).

(A5) The present embodiment is further configured such that the blood viscosity distribution calculating means 82 calculates the blood viscosity distribution DV within the blood vessel 20 under measurement on the basis of the above-described blood flow velocity distribution DS, and according to the two-dimensional or three-dimensional Navier-Stokes equations stored in a memory. Accordingly, the present invention is applicable to the blood vessel function inspecting apparatus which is practically operable.

(A6) The present embodiment is further configured such that the blood vessel diameter measuring means 96 measures the diameter change ratio (dilatation ratio R) of the blood vessel 20 after releasing of the blood vessel 20 from the blood flow obstruction, concurrently with the measurement of the blood flow velocity distribution DS by the blood flow velocity distribution measuring means 80, and the blood vessel dilatation index value calculating means 98 calculates the ratio between the maximum value $SS_{MAX}$ of the blood shear stress within the blood shear stress distribution DSS and the maximum value $R_{MAX}$ of the diameter change ratio of the blood vessel after the above-described releasing of the blood vessel from the blood flow obstruction, as one of the blood vessel dilation index values X2. Accordingly, it is possible to evaluate the result of measurement of the diameter change ratio of the above-described blood vessel 20, on the basis of the shear stress SS of the blood.

(A7) The present embodiment is further configured such that the blood vessel dilatation function abnormality detecting means 100 determines that the dilatation function of the blood vessel is abnormal, if the blood vessel dilation index value X2, which is the ratio between the maximum value $SS_{MAX}$ of the blood shear stress within the blood shear stress distribution DSS and the maximum value $R_{MAX}$ of the diameter change ratio of the blood vessel after the above-described releasing of the blood vessel from the blood flow obstruction, is outside the predetermined normal range. Accordingly, the determination as to whether the above-described blood vessel dilatation function is abnormal or not can be made more easily than in the case where the above-described blood vessel dilatation function abnormality detecting means 100 is not provided.

(A8) The present embodiment is further configured such that the ultrasonic probe 24 which emits (irradiates) the above-described ultrasonic waves toward the blood vessel 20 is provided with the long-axis ultrasonic detector array C having the plurality of ultrasonic oscillators arranged linearly in a longitudinal direction of the blood vessel 20 (a direction along $x_0$ axis), and the first short-axis ultrasonic detector array A and the second short-axis ultrasonic detector array B each having the plurality of ultrasonic oscillators arranged linearly in a direction perpendicular to the longitudinal direction of the blood vessel 20, and the blood flow velocity distribution DS is measured with the ultrasonic waves irradiated from the long-axis ultrasonic detector array C, and the change ratio of the diameter of the above-described blood vessel 20 is measured with the ultrasonic waves irradiated from the first short-axis ultrasonic detector array A. Accordingly, it is possible to implement the measurement of the above-described blood low velocity distribution DS and the measurement of the change ratio of the diameter of the above-described blood vessel 20, concurrently with each other, by using the ultrasonic probe 24 practically used in the art. In the present embodiment, the blood flow velocity distribution DS and the change ratio of the diameter of the above-described blood vessel 20 may be measured by the long-axis ultrasonic detector array C, without using the first short-axis ultrasonic detector array A, such that the operation to measure the blood flow velocity distribution DS and the operation to measure the change ratio of the diameter of the above-described blood vessel 20 are alternately performed with an extremely short cycle time. This modification has the same advantage as described above.

While the embodiment of the present invention has been described in detail by reference to the drawings, for illustrative purpose only, it is to be understood that the invention may be embodied with various changes and improvements which may occur to those skilled in the art.

For instance, the electronic control device 28 used in the illustrated embodiment may be configured to once store, in a memory device, the data obtained by the measurements with the ultrasonic waves, and to implement arithmetic operations after completion of the measurements, or to alternatively implement the arithmetic operations concurrently with the measurements.

In the illustrated embodiment, the blood vessel dilatation index value calculating means 98 calculates, as one of the above-described blood vessel dilatation index values X2, the ratio between the maximum blood shear stress value $SS_{MAX}$ and the maximum blood vessel diameter change ratio value $R_{MAX}$ after the blood vessel releasing from the blood flow obstruction. However, the maximum blood vessel diameter change ratio value $R_{MAX}$ after the blood vessel releasing from the blood flow obstruction may be replaced by another other parameter such as (i) a maximum value (unit: mm, for example) of an amount of change of the diameter of the blood vessel 20 after the blood vessel releasing, (ii) a delay time from the point of time t1 in FIG. 4 at which the blood vessel is released from the blood flow obstruction, to the point of time t2 at which the dilatation of the blood vessel 20 is initiated, or (iii) a transfer function where an input is selected from an amount or ratio of change of the diameter of the blood vessel 20 or a time constant of the diameter change, while an output is selected from the blood flow velocity, a flow rate of the blood, the blood shear rate SR or the blood shear stress SS, or vice versa.

Although the electronic control device 28 provided in the illustrated embodiment is provided with the blood vessel dilatation function evaluating means 76, the electronic control device 28 may not be provided with this evaluating means 76. Where the electronic control device 28 is not provided with the blood vessel dilatation function evaluating means 76, the shear stress distribution calculating means 86 need not be provided.

While the electronic control device 28 provided in the illustrated embodiment is provided with the blood state abnormality detecting means 94 and the blood vessel dilatation function abnormality detecting means 100, one or both of these detecting means 94, 100 may not be provided.

The brachium 16 shown in FIG. 1 in the illustrated embodiment is the brachium of the human body, for example.

In the illustrated embodiment, the blood vessel diameter measuring means 96 measures the blood vessel lumen diameter $d_1$ on the basis of the image synthesized on the basis of the reflected waves received by the first short-axis ultrasonic detector array A of the ultrasonic probe 24. However, the blood vessel diameter measuring means 96 may be configured to measure the blood vessel lumen diameter $d_1$ on the basis of the image synthesized on the basis of the reflected waves received by the long-axis ultrasonic detector array C of the ultrasonic probe 24.

It is to be understood that the present invention may be embodied with various other changes not illustrated herein, without departing from the spirit of this invention.

NOMENCLATURE OF REFERENCE SIGNS

14: Live body
20: Blood vessel
22: Blood vessel function inspecting apparatus
24: Ultrasonic probe
82: Blood viscosity distribution calculating means
86: Shear stress distribution calculating means
90: First blood state index value calculating means
92: Second blood state index value calculating means
94: Blood state abnormality detecting means
96: Blood vessel diameter measuring means
98: Blood vessel dilatation index value calculating means
100: Blood vessel dilatation function abnormality detecting means
A: First short-axis ultrasonic detector array (Transverse ultrasonic detector array)
C: Long-axis ultrasonic detector array (Longitudinal ultrasonic detector array)

The invention claimed is:

1. A blood vessel function inspecting apparatus comprising:

an ultrasonic probe for irradiating ultrasonic waves and detecting reflected ultrasonic waves, wherein the irradiated ultrasonic waves are percutaneously incident upon a blood vessel of a live body;

a processor having a program stored therein for causing the processor to perform executable portions, the portions comprising:

a blood viscosity distribution calculating portion and a shear rate distribution calculating portion respectively configured to calculate a blood viscosity distribution and a shear rate distribution of blood within the blood vessel of the live body on the basis of a flow velocity distribution of the blood measured in a non-invasive manner with the ultrasonic waves percutaneously incident upon said blood vessel, and a blood state index value calculating portion configured to calculate a blood state index value permitting evaluation of a state of the blood, on the basis of said blood viscosity distribution and said shear rate distribution, comprising:

a first blood state index value calculating portion configured to obtain estimated hematocrit values at a plurality of points predetermined within said blood vessel, on the basis of values of a blood viscosity at said plurality of points, which are respectively extracted from said blood viscosity distribution and according to reference relationships between a hematocrit value and the blood viscosity, which reference relationships respectively correspond to values of a shear rate at said plurality of points, which are respectively extracted from said shear rate distribution; and a second blood state index value calculating portion configured to calculate, as said blood state index value, a value relating to an amount of difference of the estimated hematocrit values at said plurality of points with respect to each other, in which the estimated hematocrit values are obtained from said reference relationships that are transformed at a same ratio so as to minimize the amount of difference of the estimated hematocrit values, wherein said second blood state index value calculating portion transforms said reference relationships at the same ratio for all of the values of the shear rate, by changing relationship equations respectively defining said reference relationships corresponding to the respective different values of the shear rate, with a same coefficient, and determines, as said blood state index value, said coefficient when the amount of difference of the estimated hematocrit values at said plurality of points is minimized.

2. The blood vessel function inspecting apparatus according to claim 1, wherein said second blood state index value calculating portion is configured to calculate a second blood state index value, wherein said second blood state index value is calculated as an average of the estimated hematocrit values at said plurality of points.

3. The blood vessel function inspecting apparatus according to claim 1, wherein said second blood state index value calculating portion is configured to calculate a second blood state index value, said second blood state index value calculated as an average of differences of the estimated hematocrit values at said plurality of points with respect to a predetermined reference hematocrit value when the amount of difference of the estimated hematocrit values at said plurality of points is minimized, the executable portions further comprising a blood state abnormality detecting portion configured to determine that said blood state is abnormal, if the average of the differences of the estimated hematocrit values at said plurality of points with respect to said reference hematocrit value is larger than a threshold value.

4. The blood vessel function inspecting apparatus according to claim 1, wherein said blood viscosity distribution calculating portion is configured to calculate said blood viscosity distribution on the basis of said flow velocity distribution of the blood, and according to a two-dimensional or three-dimensional Navier-Stokes equation stored in a memory.

5. A blood vessel function inspecting apparatus comprising:

an ultrasonic probe for irradiating ultrasonic waves and detecting reflected ultrasonic waves, wherein the irradiated ultrasonic waves are percutaneously incident upon a blood vessel of a live body;

a processor having a program stored therein for causing the processor to perform executable portions, the portions comprising:

a blood viscosity distribution calculating portion and a shear rate distribution calculating portion respectively configured to calculate a blood viscosity distribution and a shear rate distribution of blood within the blood vessel of the live body on the basis of a flow velocity distribution of the blood measured in a non-invasive manner with the ultrasonic waves percutaneously incident upon said blood vessel, and a blood state index value calculating portion configured to calculate a blood state index value permitting evaluation of a state of the blood, on the basis of said blood viscosity distribution and said shear rate distribution, comprising:

a first blood state index value calculating portion configured to obtain estimated hematocrit values at a plurality of points predetermined within said blood vessel, on the basis of values of a blood viscosity at said plurality of points, which are respectively extracted from said blood viscosity distribution, and according to reference relationships between a hematocrit value and the blood viscosity, which reference relationships respectively correspond to values of a shear rate at said plurality of points, which are respectively extracted from said shear rate distribution;

a second blood state index value calculating portion configured to calculate, as said blood state index value, a value relating to an amount of difference of the estimated hematocrit values at said plurality of points with respect to each other, in which the estimated hematocrit values are obtained from said reference relationships which are transformed at a same ratio so as to minimize the amount of difference of the estimated hematocrit values;

a blood vessel diameter measuring portion configured to measure a change ratio of a diameter of said blood vessel after releasing of the blood vessel from blood flow obstruction, concurrently with the measurement of said flow velocity distribution of the blood within said blood vessel with said ultrasonic waves incident upon the blood vessel;

a shear stress calculating portion configured to calculate a shear stress distribution on the basis of said blood viscosity distribution and said shear rate distribution of the blood; and a blood vessel dilatation index value calculating portion configured to calculate a ratio between a maximum value of the shear stress within said shear stress distribution and a maximum value of said change ratio of the diameter of the blood vessel, as a blood vessel dilation index value permitting evaluation of a dilatation function of the blood vessel.

6. The blood vessel function inspecting apparatus according to claim 5, wherein the executable portions further comprise a blood vessel dilatation function abnormality detecting portion configured to determine that said dilatation function of the blood vessel is abnormal, if said blood vessel dilation index value is outside a predetermined normal range.

7. The blood vessel function inspecting apparatus according to claim 5, wherein the ultrasonic probe which irradiates said ultrasonic waves toward said blood vessel is provided with a longitudinal ultrasonic detector array having a plurality of ultrasonic oscillators arranged linearly in a longitudinal direction of said blood vessel, and a transverse ultrasonic detector array having a plurality of ultrasonic oscillators arranged linearly in a direction perpendicular to the longitudinal direction of said blood vessel, and wherein said flow velocity distribution of the blood is measured with the ultrasonic waves irradiated from said longitudinal ultrasonic detector array, and the change ratio of the diameter of said blood vessel is measured with the ultrasonic waves irradiated from said transverse ultrasonic detector array.

8. The blood vessel function inspecting apparatus according to claim 5, wherein the ultrasonic probe which irradiates said ultrasonic waves toward said blood vessel is provided with a longitudinal ultrasonic detector array having a plurality of ultrasonic oscillators arranged linearly in a longitudinal direction of said blood vessel, and wherein an operation of said longitudinal ultrasonic detector array to measure the flow velocity distribution of the blood and an operation of the longitudinal ultrasonic detector array to measure the change ratio of the diameter of said blood vessel are alternately performed with time.

* * * * *